(12) United States Patent
Patel et al.

(10) Patent No.: US 10,981,007 B2
(45) Date of Patent: Apr. 20, 2021

(54) SYSTEMS, METHODS, AND DEVICES FOR NEUROMODULATION

(71) Applicant: Georgia Tech Research Corporation, Atlanta, GA (US)

(72) Inventors: Yogi Anil Patel, Baltimore, MD (US); Ravi V. Bellamkonda, Atlanta, GA (US); Robert Butera, Decatur, GA (US); Tarun Saxena, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 136 days.

(21) Appl. No.: 16/301,054

(22) PCT Filed: May 12, 2017

(86) PCT No.: PCT/US2017/032418
§ 371 (c)(1),
(2) Date: Nov. 13, 2018

(87) PCT Pub. No.: WO2017/197272
PCT Pub. Date: Nov. 16, 2017

(65) Prior Publication Data
US 2019/0184166 A1    Jun. 20, 2019

Related U.S. Application Data

(60) Provisional application No. 62/335,722, filed on May 13, 2016.

(51) Int. Cl.
*A61N 1/36*    (2006.01)
*A61N 1/05*    (2006.01)
(Continued)

(52) U.S. Cl.
CPC ........ *A61N 1/36053* (2013.01); *A61B 5/0488* (2013.01); *A61B 5/0492* (2013.01);
(Continued)

(58) Field of Classification Search
CPC ...... A61N 1/0551; A61N 1/0556; A61N 1/06; A61N 1/18; A61N 1/32; A61N 1/36;
(Continued)

(56) References Cited

U.S. PATENT DOCUMENTS 5,231,988 A   8/1993   Wernicke et al.
6,135,978 A  10/2000   Houben et al.
(Continued)

FOREIGN PATENT DOCUMENTS

WO   2004054606   7/2004
WO   2009124233   10/2009

OTHER PUBLICATIONS

Patel YA, Butera RJ. Differential fiber-specific block of nerve conduction in mammalian peripheral nerves using kilohertz electrical stimulation. J Neurophysiol. 2015;113(10):3923-3929. doi:10.1152/jn.00529.2014.*

(Continued)

*Primary Examiner* — Eugene T Wu
(74) *Attorney, Agent, or Firm* — Meunier Carlin & Curfman LLC

(57) ABSTRACT

Systems, methods, and devices for neuromodulation are described herein. For example, a method for modulating inflammatory processes of a subject is described. The method can include stimulating the subject's vagus nerve to activate an efferent pathway, and stimulating the subject's vagus nerve to inhibit neural activity. Pairing activation of the efferent pathway and inhibition of neural activity can enhance an anti-inflammatory response of the subject.

21 Claims, 10 Drawing Sheets

(51) Int. Cl.
| | |
|---|---|
| A61N 1/365 | (2006.01) |
| A61N 1/32 | (2006.01) |
| A61N 1/18 | (2006.01) |
| A61N 1/00 | (2006.01) |
| A61B 5/0488 | (2006.01) |
| A61B 5/0492 | (2006.01) |
| A61B 5/00 | (2006.01) |

(52) U.S. Cl.
CPC .......... *A61B 5/4035* (2013.01); *A61B 5/4836* (2013.01); *A61N 1/00* (2013.01); *A61N 1/05* (2013.01); *A61N 1/18* (2013.01); *A61N 1/32* (2013.01); *A61N 1/36* (2013.01); *A61N 1/365* (2013.01); *A61N 1/3606* (2013.01)

(58) Field of Classification Search
CPC .............. A61N 1/3605; A61N 1/36053; A61N 1/36057; A61N 1/3606; A61N 1/36121
See application file for complete search history.

(56) References Cited

U.S. PATENT DOCUMENTS

| | | | |
|---|---|---|---|
| 8,060,208 | B2 | 11/2011 | Kilgore et al. |
| 8,504,161 | B1* | 8/2013 | Kornet ................ A61N 1/36053 607/118 |
| 2003/0181958 | A1 | 9/2003 | Dobak, III |
| 2004/0243182 | A1* | 12/2004 | Cohen .................. A61N 1/0556 607/2 |
| 2006/0190053 | A1 | 8/2006 | Dobak |
| 2006/0287678 | A1 | 12/2006 | Shafer |
| 2007/0106337 | A1 | 5/2007 | Errico et al. |
| 2009/0254143 | A1 | 10/2009 | Tweden et al. |
| 2010/0191311 | A1* | 7/2010 | Scheiner .............. A61N 1/0556 607/62 |
| 2013/0158618 | A1 | 6/2013 | Libbus et al. |
| 2013/0345591 | A1 | 12/2013 | Hincapie Ordonez et al. |
| 2014/0296940 | A1* | 10/2014 | Gross .................. A61N 1/36157 607/62 |
| 2015/0202433 | A1* | 7/2015 | Franke ................. A61N 1/0556 607/72 |
| 2016/0001082 | A1* | 1/2016 | Butera ............... A61N 1/36057 607/66 |
| 2016/0256683 | A1 | 9/2016 | Butera et al. |

OTHER PUBLICATIONS

Bhadra, N. and Kilgore, K.L. (2005), High-frequency electrical conduction block of mammalian peripheral motor nerve. Muscle Nerve, 32: 782-790. doi:10.1002/mus.20428.*
Patel YA, Butera RJ. Challenges associated with nerve conduction block using kilohertz electrical stimulation. J Neural Eng. 2018; 15(3):031002. doi:10.1088/1741-2552/aaadc0.*
Borovikova LV, Ivanova S, Zhang M, et al. Vagus nerve stimulation attenuates the systemic inflammatory response to endotoxin. Nature. 2000;405(6785):458-462. doi:10.1038/35013070.*
Patel, Y., Saxena, T., Bellamkonda, R. et al. Kilohertz frequency nerve block enhances anti-inflammatory effects of vagus nerve stimulation. Sci Rep 7, 39810 (2017). https://doi.org/10.1038/srep39810.*
International Search Report and Written Opinion dated Aug. 2, 2017, from International Application No. PCT/US2017/032418, 10 pages.
Borovikova, L. V. et al. "Vagus nerve stimulation attenuates the systemic inflammatory response to endotoxin", Nature 405, 458-462 (2000).
Rosas-Ballina, M. et al. "Splenic nerve is required for cholinergic antiinflammatory pathway control of TNF in endotoxemia", Proceedings of the National Academy of Sciences of the United States of America 105, 11008-11013 (2008).
Martelli, D. et al. "The cholinergic anti-inflammatory pathway: A critical review", Autonomic Neuroscience: Basic and Clinical 182, 65-69 (2014).
Prechtl, J. C. et al. "The fiber composition of the abdominal vagus of the rat", Anatomy and Embryology 181, 101-115 (1990).
Powley, T. L. et al. "Anatomical considerations for surgery of the rat abdominal vagus: distribution, paraganglia and regeneration", Journal of the Autonomic Nervous System 9, 79-97 (1983).
Berthoud, H.-R. et al. "Characterization of vagal innervation to the rat celiac, suprarenal and mesenteric ganglia", Journal of the Autonomic Nervous System 42, 153-169 (1993).
Patel, Y. A. et al. "Differential fiber-specific block of nerve conduction in mammalian peripheral nerves using kilohertz electrical stimulation", Journal of Neurophysiology 113, 3923-3929 (2015).
Hosoi, T. et al. "Electrical stimulation of afferent vagus nerve induces IL-1beta expression in the brain and activates HPA axis", American Journal of Physiology Regulatory, Integrative and Comparative Physiology 279, R141-R147 (2000).
Martelli, D. et al. "Neural control of inflammation by the greater splanchnic nerves", Temperature 1, 14-15 (2014).
Bratton, B. O. et al. "Neural regulation of inflammation: no neural connection from the vagus to splenic sympathetic neurons", Experimental Physiology 97, 1180-1185 (2012).
Martelli, D. et al. "Reflex control of inflammation by sympathetic nerves, not the vagus", The Journal of Physiology 592, 1677-1686 (2014).
Labiner, D. M. et al. "Vagus nerve stimulation therapy in depression and epilepsy: therapeutic parameter settings", Acta neurologica scandinavica 115, 23-33 (2007).
Koopman, F. A. et al. "Vagus nerve stimulation inhibits cytokine production and attenuates disease severity in rheumatoid arthritis", Proceedings of the National Academy of Sciences 113, 8284-8289 (Jul. 2016).
Laviano, A. et al. "Neural control of the anorexia-cachexia syndrome", American Journal of Physiology Endocrinology and Metabolism 295, 1000-1008 (2008).
Brooks, S. L. et al. "Sympathetic activation of brown-adipose-tissue thermogenesis in cachexia", Bioscience Reports 1, 509-517 (1981).
Joseph, L. et al. "High-frequency stimulation selectively blocks different types of fibers in frog sciatic nerve", IEEE Transactions on Neural Systems and Rehabilitation Engineering 19, 550-557 (2011).
Agostoni, E. et al. "Functional and histological studies of the vagus nerve and its branches to the heart, lungs and abdominal viscera in the cat", The Journal of Physiology 135, 182-205 (1957).
Franke, M. et al. "Direct current contamination of kilohertz frequency alternating current waveforms", Journal of Neuroscience Methods 232, 74-83 (2014).
Miles, J. D. et al. "Effects of ramped amplitude waveforms on the onset response of high-frequency mammalian nerve block", Journal of Neural Engineering 4, 390-398 (2007).
Willemze, R. A. et al. "Neural reflex pathways in intestinal inflammation: hypotheses to viable therapy", Nature Reviews Gastroenterology & Hepatology 12, 353-362 (2015).
Nance, D. M. et al. "Autonomic Innervation and Regulation of the Immune System (1987-2007)", Brain, Behavior, and Immunity 21,736-745 (2007).
Huston, J. M. et al. "Splenectomy inactivates the cholinergic antiinflammatory pathway during lethal endotoxemia and polymicrobial sepsis", The Journal of Experimental Medicine 203,1623-1628 (2006).
Lin, R. J. et al. "Real-time Experiment Interface for biological control applications", In 2010 Annual International Conference of the IEEE Engineering in Medicine and Biology Society, EMBC'10, 4160-4163 (2010).
Yoo, P. B. et al. "High-resolution measurement of electrically-evoked vagus nerve activity in the anesthetized dog", Journal of Neural Engineering 10, 1-9 (2013).
Chu, J.-U. et al. "Improvement of signal-to-interference ratio and signal-to-noise ratio in nerve cuff electrode systems", Physiological Measurement 33, 943-967 (2012).
Olofsson, P.S. et al. "Single-Pulse and Unidirectional Electrical Activation of the Cervical Vagus Nerve Reduces Tumor Necrosis Factor in Endotoxemia", Bioelectronic Medicine, 2:37-42, 2015.

(56) References Cited

OTHER PUBLICATIONS

Niijima A., "Control of liver function and neuroendocrine regulation of blood glucose levels, Integrative Functions of the autonomic nervous system; an analysis of the interrelationships and interactions of the sympathetic and parasympathetic," 1979, pp. 68-83. (9 pages).

Berthoud, H.-R. et al., "Characteristics of gastric and pancreatic responses to vagal stimulation with varied frequencies: evidence for different fiber calibers?," Journal of the Autonomic Nervous System, 1987, vol. 19, pp. 77-34. (8 pages).

Jungermann, K. et al., "Regulation of liver metabolism by the hepatic nerves," Advances in Enzyme Regulation, 1987, pp. 63-88. (27 pages).

Bhadra, N. et al., "High-Frequency Electrical Conduction Block of Mammalian Peripheral Motor Nerve," Muscle Nerve, 2005, vol. 32, pp. 782-790. (9 pages).

Bhadra, N. et al., "High frequency electrical conduction block of the pudendal nerve," J. Neural Eng., 2006, vol. 3, pp. 180-187. (8 pages).

ClinicalTrials.gov; Identifier: NCT01117311; Vagal Nerve Stimulation and Glucose Metabolism (2013).

\* cited by examiner

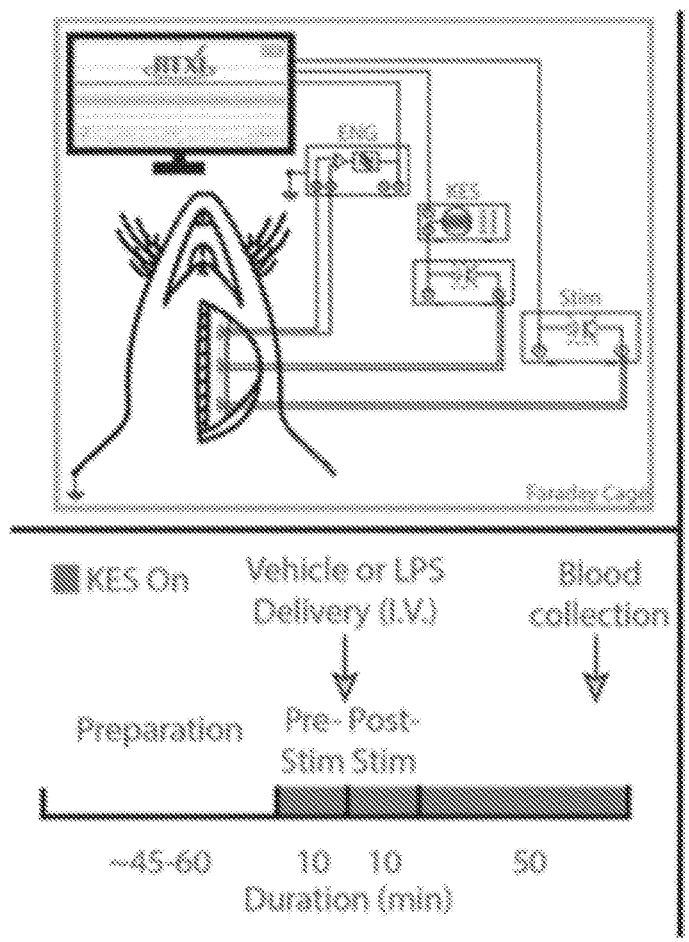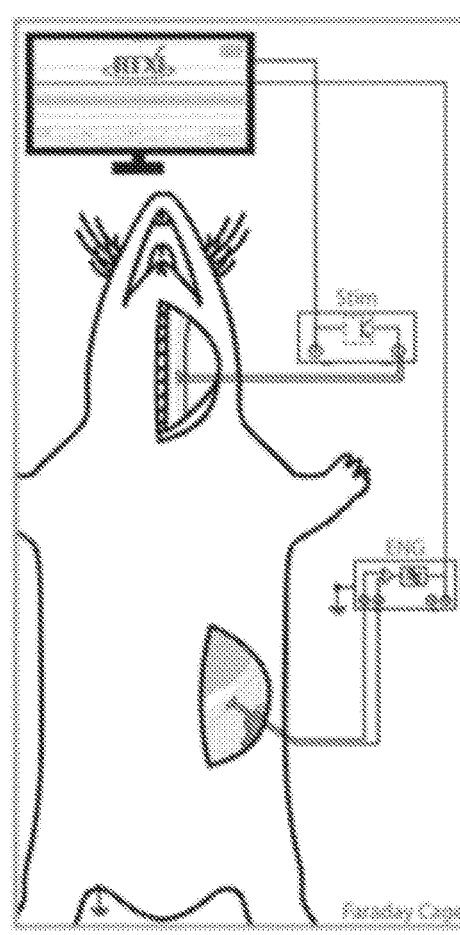
FIG. 6A  FIG. 6B
FIG. 6C

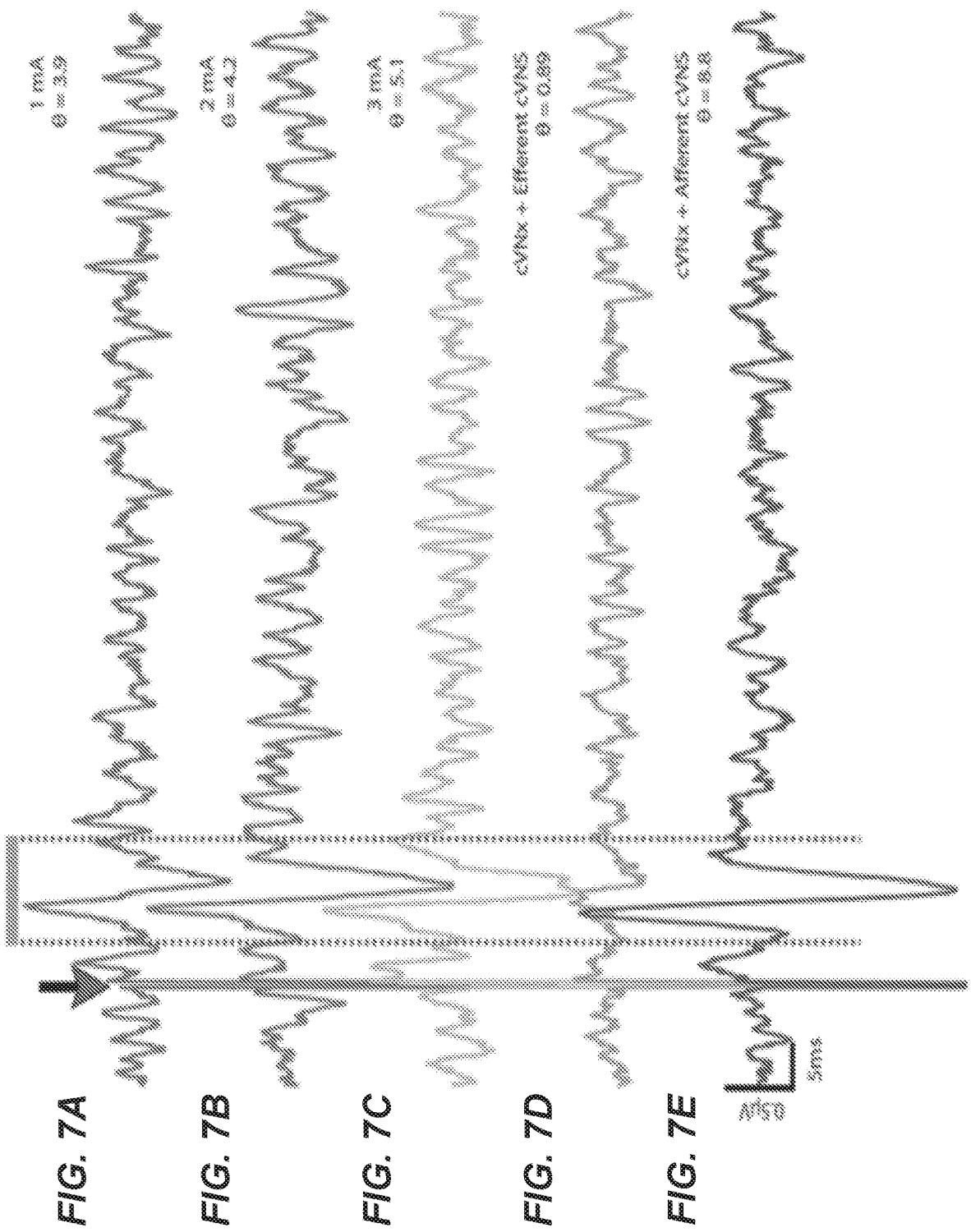

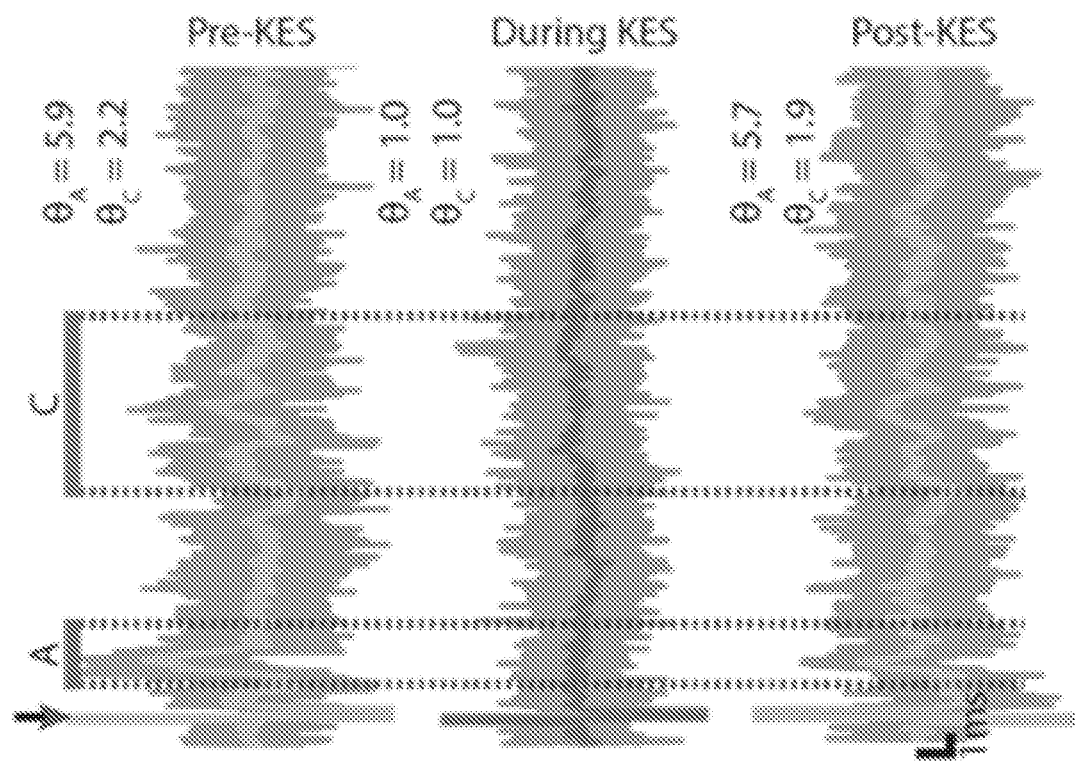
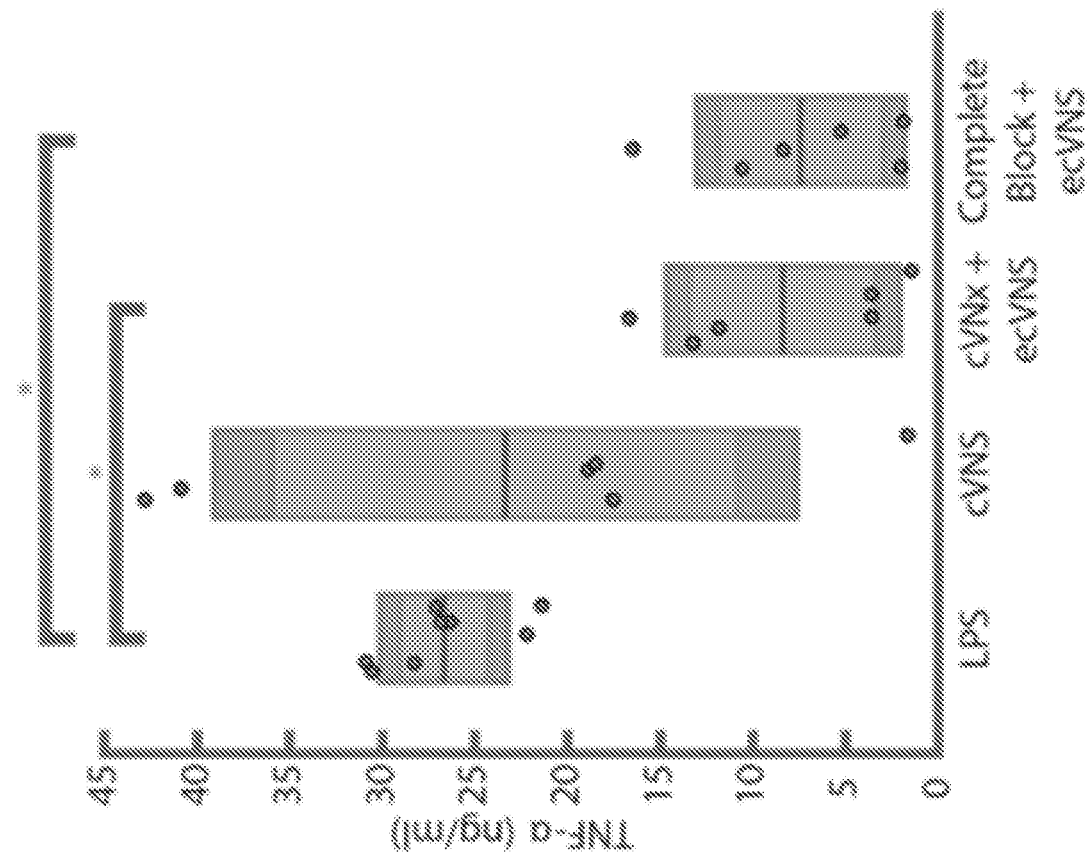
FIG. 8A
FIG. 8B

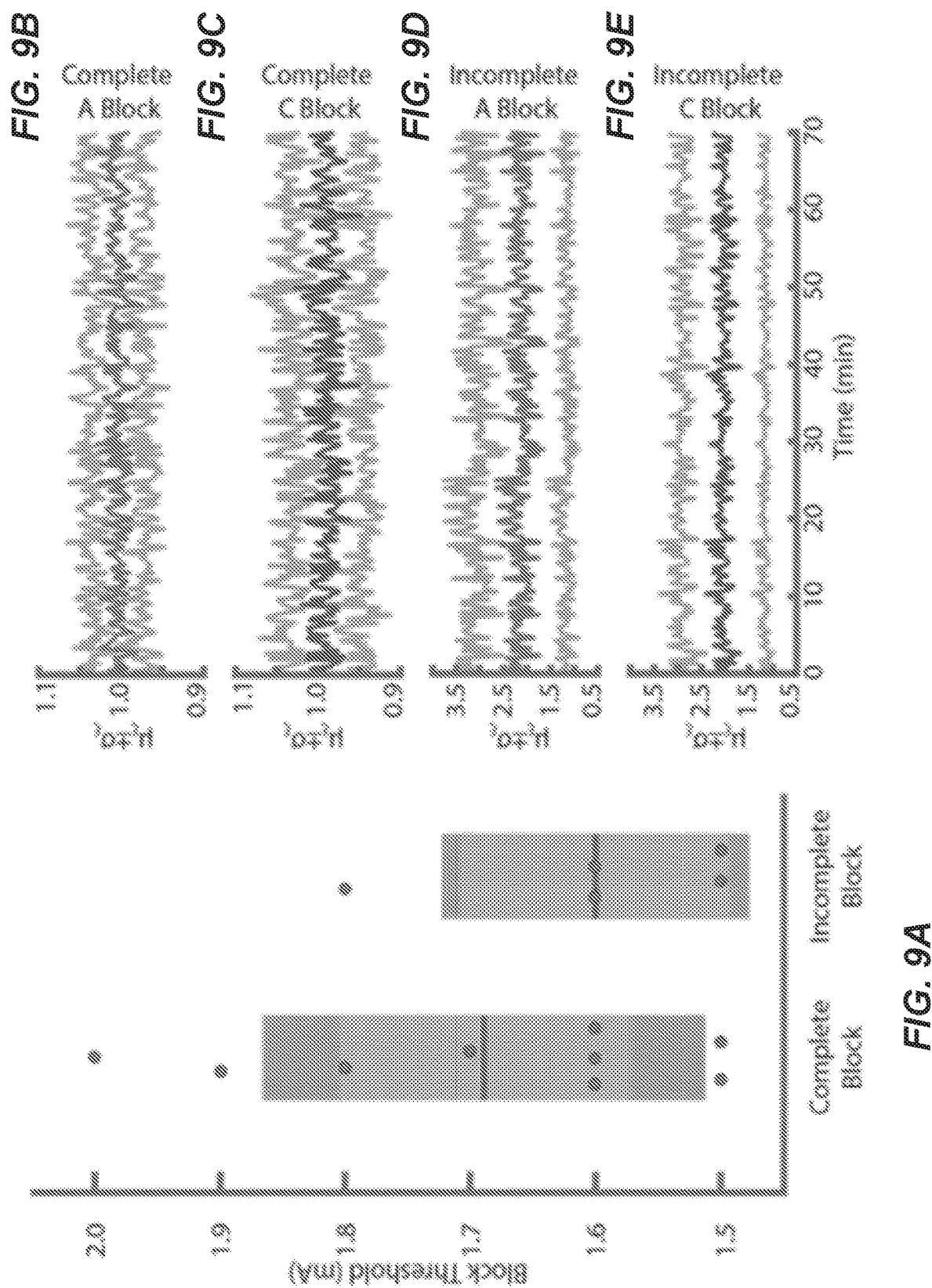

SYSTEMS, METHODS, AND DEVICES FOR NEUROMODULATION

CROSS-REFERENCE TO RELATED APPLICATIONS

This application is a national stage application filed under 35 U.S.C. 0371 of PCT/US2017/032418 filed May 12,2017, which claims the benefit of U.S. provisional patent application No. 62/335,722, filed on May 13, 2016, and entitled "OPTIMIZED NEUROMODULATION OF VAGAL STIMULATION FOR INFLAMMATORY MODULATION," the disclosure of which are expressly incorporated herein by reference in their entireties.

STATEMENT REGARDING FEDERALLY FUNDED RESEARCH

This invention was made with government support under Grant no. 2R01EB016407-09A1 awarded by the National Institutes of Health. The government has certain rights in the invention.

BACKGROUND

Activation, inhibition, and control of the innate immune system is vital for maintenance of homeostasis in living organisms, and one in which both the central nervous system (CNS) and peripheral nervous systems (PNS) play a critical role. The CNS actively responds to acute immune challenges by altering body temperature, stimulating the hypothalamic-pituitary-adrenal (HPA) axis, as well as up- and down-regulating specific sympathetic pathways, which are primarily involved in attenuating both cellular and humoral responses initiated by an immune challenge. The PNS enables modulation of the response to an immune challenge by allowing directional stimulation of nerves involved in signaling between the CNS and effector peripheral targets (e.g., ganglia, organs, tissues). Studies from over the last two decades have highlighted the ability to modulate the systemic response to an immune challenge, both in animal and clinical investigations, by electrical stimulation of the cVN.

Studies first conducted by Borovikova et al. demonstrated down regulation of the systemic response to lethal endotoxemia in rats by electrically stimulating the efferent pathways in the cVN. Borovikova et al. achieved the systemic response by stimulating the distal end of the transected cervical vagus nerve (cVN). (Reference 1). Their results demonstrated the direct influence of the response to an incoming and ongoing acute immune challenge via electrical stimulation. These initial findings have led to a significant number of investigations aimed at the use of cervical vagus nerve stimulation (cVNS) for modulation of inflammation in a variety of clinical conditions (ClinicalTrials.gov Identifiers: NCT01552941, NCT02311660). Continued investigations into the mechanism of action have engendered the cholinergic anti-inflammatory pathway. (Reference 2). Martelli et al. provides a critical review of the cholinergic anti-inflammatory pathway. (Reference 3).

Although the mechanism is unknown and requires significant inquiry, results from both animal and initial clinical investigations posit a potential benefit of efferent cVNS in ameliorating systemic and local inflammation. Many, if not all, cVNS investigations stimulate the intact cVN, leading to activation of both afferent and efferent pathways, or achieve selective stimulation of an afferent or efferent pathway by transecting the nerve. While these approaches are sufficient for elucidating acute effects in animal investigations, clinical translation of selective afferent (acVNS) or efferent cVNS (ecVNS) requires a safe and effective alternative approach. Various studies have investigated the ability to selectively stimulate via custom electrode geometries and different stimulation waveforms. These approaches suffer from clinical challenges such as patient-to-patient variations in nerve anatomy as well as surgical placement and movement of electrodes. Furthermore, a cervical vagotomy (i.e., nerve transection) is not desirable in clinical settings due to the fact that a significant amount of parasympathetic control is exerted on the visceromotor systems through the vagi. (References 4-6). A safe, effective, and reversible selective acVNS or ecVNS method is clearly necessary for controlling inflammation in humans.

SUMMARY

Systems, methods, and devices for neuromodulation are described herein. For example, a method for modulating inflammatory processes of a subject is described. The method can include stimulating the subject's vagus nerve to activate an efferent pathway, and stimulating the subject's vagus nerve to inhibit neural activity. Pairing activation of the efferent pathway and inhibition of neural activity can enhance an anti-inflammatory response of the subject.

Alternatively or additionally, the stimulation to inhibit neural activity can achieve a complete block of the subject's vagus nerve. Optionally, the complete block of the subject's vagus nerve can be a nerve block equivalent to a nerve transection.

Alternatively or additionally, the stimulation to inhibit neural activity can be configured to alter a membrane potential of the subject's vagus nerve.

Alternatively or additionally, pairing activation of the efferent pathway and inhibition of neural activity can balance anti-inflammatory and pro-inflammatory responses of the subject.

Alternatively or additionally, the method can optionally further include treating a disease or condition of the subject.

Alternatively or additionally, stimulating the subject's vagus nerve to activate the efferent pathway can include applying at least one of infrared, electrical, thermal, optical, or chemical stimulation. In some implementations, this stimulation includes applying electrical stimulation.

Alternatively or additionally, stimulating the subject's vagus nerve to inhibit neural activity can include applying at least one of infrared, electrical, thermal, optical, or chemical stimulation. In some implementations, this stimulation includes applying kilohertz electrical stimulation (KES). Optionally, the KES can have a frequency from about 1 kHz to about 100 kHz. Optionally, the KES can have a frequency from about 5 kHz to about 50 kHz. Optionally, the KES can deliver a current with an amplitude from about 50 μA to about 50 mA. Optionally, the KES can deliver a current with an amplitude from about 100 μA to about 20 mA.

Alternatively or additionally, the subject's vagus nerve can be stimulated to activate the efferent pathway during a first period of time, and the subject's vagus nerve can be stimulated to inhibit neural activity during a second period of time. Optionally, in some implementations, the first period of time and the second period of time at least partially overlap. For example, the first period of time and the second period of time can optionally be simultaneous periods of time. In other implementations, the first period of time and the second period of time can be different, non-overlapping periods of time.

An example device for modulating inflammatory processes of a subject is also described herein. The device can include a first probe configured to interface with the subject's vagus nerve, a second probe configured to interface with the subject's vagus nerve, a stimulus generator operably coupled with the first probe and the second probe, and a control unit operably coupled with the stimulus generator. The stimulus generator can be configured to provide stimulus signals to the first probe and the second probe. Additionally, the control unit, which can include a processor and memory, can be configured to control the stimulus generator to provide a first stimulus signal configured to activate an efferent pathway of the subject's vagus nerve, and provide a second stimulus signal configured to inhibit neural activity of the subject's vagus nerve. Pairing activation of the efferent pathway and inhibition of neural activity can enhance an anti-inflammatory response of the subject.

In some implementations, the first probe and the second probe can be different probes. Optionally, the first and second probes can be electrodes.

Another example method for neuromodulation is also described herein. The method can include stimulating a subject's nerve to inhibit neural activity, stimulating the subject's nerve to activate neural activity, and controlling the paired stimulation that inhibits and activates neural activity to selectively activate at least one of efferent or afferent neural activity. The stimulation to inhibit neural activity can be configured to alter a membrane potential of the subject's nerve.

Alternatively or additionally, selectively activating at least one of efferent or afferent neural activity can modulate physiological processes of the subject. In some implementations, the method can optionally further include treating a disease or condition of the subject by modulating the physiological processes of the subject.

Alternatively or additionally, the subject's nerve can be a central nerve or a peripheral nerve including, but not limited to, the greater splanchnic nerve, the subdiaphragmatic/abdominal vagus nerve, the median nerve, the ulnar nerve, the sciatic nerve, the sympathetic chain, or the dorsal/spinal roots.

Alternatively or additionally, the method can optionally further include balancing the physiological processes of the subject. For example, the efferent and afferent neural activity can be balanced. In some implementations, the method can optionally further include treating a disease or condition of the subject by balancing the physiological processes of the subject.

Alternatively or additionally, stimulating the subject's nerve to activate neural activity comprises applying at least one of infrared, electrical, thermal, optical, or chemical stimulation. In some implementations, this stimulation includes applying electrical stimulation.

Alternatively or additionally, in some implementations, stimulating the subject's nerve to activate neural activity includes applying distal stimulation to activate efferent neural activity. In other implementations, stimulating the subject's nerve to activate neural activity comprises applying proximal stimulation to activate afferent neural activity.

Alternatively or additionally, stimulating the subject's nerve to inhibit neural activity comprises applying at least one of infrared, electrical, thermal, optical, or chemical stimulation. In some implementations, this stimulation includes applying kilohertz electrical stimulation (KES).

Another example device for neuromodulation is also described herein. The device can include a first probe configured to interface with a subject's nerve, a second probe configured to interface with the subject's nerve, a stimulus generator operably coupled with the first probe and the second probe, and a control unit operably coupled with the stimulus generator. The stimulus generator can be configured to provide stimulus signals to the first probe and the second probe. Additionally, the control unit, which can include a processor and memory, can be configured to control the stimulus generator to provide a first stimulus signal configured to inhibit neural activity of the subject's nerve, provide a second stimulus signal configured to activate neural activity of the subject's nerve, and control the paired stimulation that inhibits and activates neural activity to selectively activate at least one of efferent or afferent neural activity. The stimulation to inhibit neural activity can be configured to alter a membrane potential of the subject's nerve.

Yet another method for neuromodulation is described herein. The method can include stimulating a subject's nerve using kilohertz electrical stimulation (KES) to inhibit neural activity, stimulating the subject's nerve to activate at least one of efferent or afferent neural activity, and controlling the paired stimulation that inhibits and activates neural activity to selectively activate at least one of efferent or afferent neural activity.

In some implementations, selectively activating at least one of efferent or afferent neural activity further includes balancing efferent and afferent neural activity. The method can optionally further include treating a disease or condition of the subject by balancing efferent and afferent neural activity.

Alternatively or additionally, in some implementations, stimulating the subject's nerve to activate neural activity includes applying distal stimulation to activate efferent neural activity. In other implementations, stimulating the subject's nerve to activate neural activity comprises applying proximal stimulation to activate afferent neural activity.

Alternatively or additionally, stimulating the subject's nerve to activate neural activity can include applying at least one of infrared, electrical, thermal, optical, or chemical stimulation.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 1A illustrates pairing inhibition of neural activity (e.g., nerve block) and selective afferent stimulation. FIG. 1B illustrates pairing inhibition of neural activity (e.g., nerve block) and selective efferent stimulation.

FIG. 2 illustrates non-selective stimulation of afferent and efferent pathways.

FIGS. 6A-6C illustrate an experimental setup and electrophysiological configuration according to implementations described herein. FIG. 6A illustrates an experiment setup and electrophysiological configuration. The left cVN was exposed and fitted with three cuff electrodes. ENG measurements were made from the cranial end of the exposed nerve. cVNS was delivered to the caudal end of the exposed nerve, with a KES delivering electrode located cranially. FIG. 6B illustrates preparation used to measure ENG from the GSN. FIG.E 6C illustrates an experiment timeline. Nerve and electrode preparation were followed by a 10 minute stimulation (pre-stim) period, in which either cVNS or cVNS+KES were delivered to the nerve. Vehicle or LPS was injected through the lateral tail vein, followed by another 10 minute stimulation (post-stim) period. For nerve block experiments, KES was on for the entire 70 minutes. Blood was collected 50 minutes after the post-stim period for biochemical analysis.

FIGS. 7A-7E illustrate ENG measurements from experiments according to implementations described herein. cVNS activates the GSN in a synchronous and dose-dependent manner. FIGS. 7A-7C illustrate increasing stimulus intensities (1 mA, 2 mA, 3 mA) delivered to the intact left cVN. Simultaneous ENG measurements are made on the ipsilateral GSN. FIG. 7D illustrates results when the caudal end of the transected cVN is stimulated, activating efferent pathways alone. FIG. 7E illustrates results when a cVNx (i.e., cervical vagus nerve transection) is performed and the cranial end of the cVN is stimulated, activating afferent pathways. Waveforms shown are stimulus-triggered averages from 1000 stimulation trials. The arrow indicates stimulus artifact, and $\theta$ values are presented for each waveform.

FIGS. 8A and 8B illustrate TNF-$\alpha$ expression data (FIG. 8A) and ENG data (FIG. 8B) for baseline cVNS conditions. In FIG. 8A, TNF-$\alpha$ levels from animals receiving no stimulation (LPS, n=8), stimulation of the intact cVN (cVNS, n=6), vagotomized efferent cVNS (cVNx+ecVNS, n=6), and complete afferent KES nerve block with paired efferent cVNS (Complete Block+ecVNS, n=6). Asterisks denote significance between bracketed groups ($\alpha=0.05$). In FIG. 8B, representative recordings from the caudal end of the cVN pre-, during-, and post-KES delivery are shown. Average measurements (darker, center traces) are superimposed upon individual runs (grey). (A) and (C) component regions depict the windows used for quantifying nerve activation ($\theta$) and block efficacy ($\theta$) for fiber A and C components in the ENG measurements. Post-KES averages are from 10 runs only. The arrow indicates stimulus artifact.

FIGS. 9A-9E illustrate KES nerve block thresholds (FIG. 9A) and $\theta$ computations (FIGS. 9B-9E). In FIG. 9A, KES block thresholds were determined during experimental preparation. Post-hoc analysis of ENG measurements and quantification of $\theta$ led to sorting of block thresholds into complete and incomplete block groups. Experiments with trials containing $\theta$ greater than the RMS noise floor during KES delivery were categorized as incomplete block for both biochemical and electrophysiological analysis. In FIGS. 9B-9E, mean and standard deviation of $\theta$ throughout experiments with both complete afferent KES nerve block ((FIGS. 9B, 9C) n=9 from all experiments) and incomplete afferent KES nerve block ((FIGS. 9D, 9E) n=5 from all experiments). Recordings from the 70 minute experiments were parsed into 210 trials, each represented by a stimulus-triggered average waveform. The darker, center traces represent the mean from all experiments in each group, with the lighter traces representing ±1$\sigma$ in each figure. Experiments with complete afferent KES nerve block met the $\theta$ criteria, while incomplete block experiments did not.

In FIG. 10A, TNF-$\alpha$ expression from control (LPS, n=8), incomplete afferent KES nerve block and paired ecVNS (Incomplete Block+ecVNS, n=5), and complete afferent KES nerve block only (Complete Block, n=3). In FIG. 10B, ENG measurements from the caudal end of the cVN during incomplete afferent KES nerve block. Average waveforms (darker, center traces) are superimposed upon individual runs (grey), with $\theta$ presented for each CAP component. The arrow indicates stimulus artifact. This example is from an experiment in which the calibration period was successfully completed, however post-hoc analysis revealed that afferent KES nerve block was incomplete. The A fiber component is partially blocked, however not complete, and the C fiber component is unmodified compared to baseline measurements.

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. While implementations will be described for neuromodulation of the vagus nerve to modulate the subject's inflammatory response, it will become evident to those skilled in the art that the implementations are not limited thereto, but are applicable for neuromodulation of nerves to modulate other physiological processes and/or to treat a disease or condition of the subject. For example, the implementations described herein can also be used for neuromodulation of visceral, craniofacial, or spinal nerves for treatment of metabolic, cardiorespiratory, and/or musculoskeletal disorders.

Example Devices for Neuromodulation of a Subject's Nerve

Figure 1A:
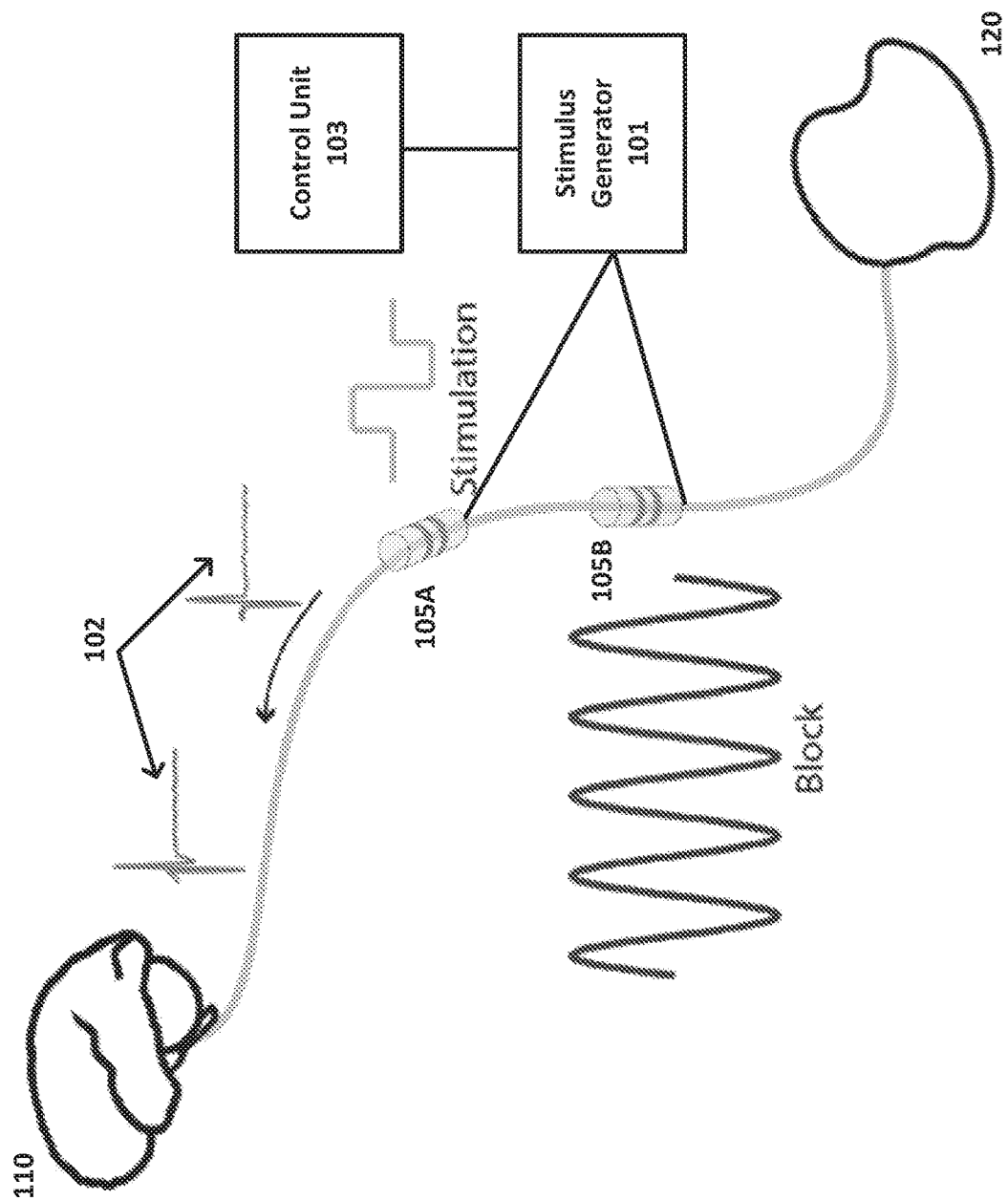
FIGS. 1A and 1B illustrate a device for neuromodulation of a subject's nerve according to implementations described herein.
Figure 1B:
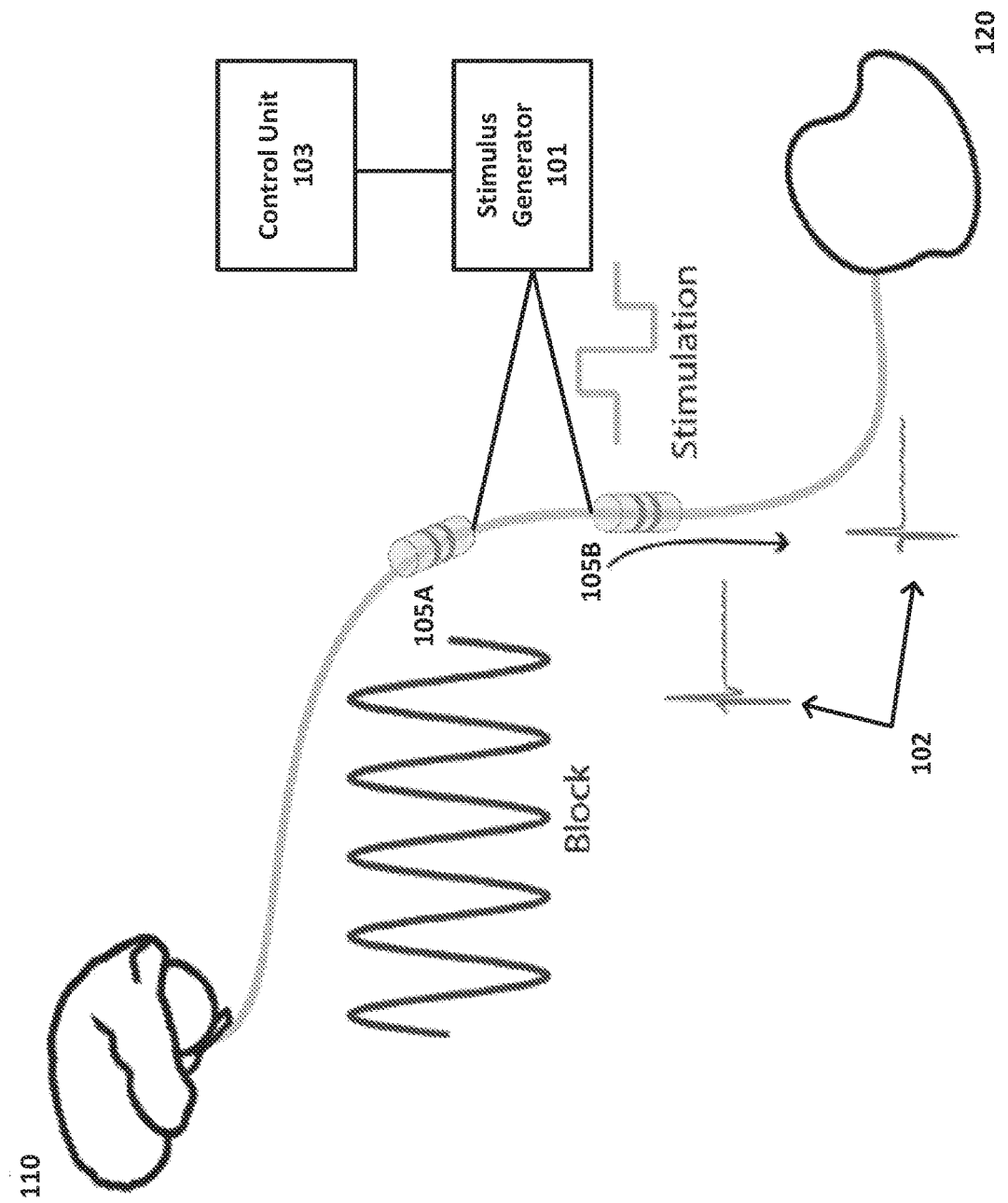

Referring now to FIGS. 1A and 1B, an example device for neuromodulation of a subject's nerve is shown. FIG. 1A illustrates pairing inhibition of neural activity (e.g., nerve block) and selective afferent stimulation. Paired stimulation (e.g., for inhibition of neural activity and selective activation of neural activity) is applied to the same nerve. As shown in FIG. 1A, neurons carry a nerve impulse 102 to the central nervous system and brain 110. FIG. 1B illustrates pairing inhibition of neural activity (e.g., nerve block) and selective efferent stimulation. Paired stimulation (e.g., for inhibition of neural activity and selective activation of neural activity) is applied to the same nerve. As shown in FIG. 1B, neurons carry a nerve impulse 102 to an organ or muscle 120 (i.e., away from the central nervous system and brain 110). The device can include a plurality of probes 105A, 105B configured to interface with the subject's nerve. As described herein, at least one probe is configured to deliver a stimulus to the subject's nerve to inhibit neural activity (e.g., inhibit both efferent and afferent pathways), and at least one probe is configured to deliver a stimulus to the subject's nerve to selectively activate the efferent or afferent pathway. As shown in FIG. 1A, probe 105A is positioned with respect to probe 105B to deliver proximal stimulation to activate afferent neural activity. As shown in FIG. 1B, probe 105B is positioned with respect to probe 105A to deliver distal stimulation to activate efferent neural activity. The probes 105A, 105B are sometimes referred to collectively herein as probes 105. This disclosure contemplates that the subject's nerve can be any nerve including, but not limited to, a central nerve (e.g., vagus nerve) or a peripheral nerve (e.g., the greater splanchnic nerve, the subdiaphragmatic/abdominal vagus nerve, the median nerve, the ulnar nerve, the sciatic nerve, the sympathetic chain, the dorsal/spinal roots, etc.). As described herein, the probes 105 can be configured to deliver at least one of infrared, electrical, thermal, optical, or chemical stimulation to the subject's nerve, for example, to inhibit or activate the subject's nerve. Optionally, the probes 105 can be implanted in the subject's body. Optionally, the probes 105 can be external to the subject's body (e.g., applied to the skin or transcutaneous).

In some implementations, the probes 105 can be electrodes configured to deliver an electrical stimulus to the subject's nerve. Each of the electrodes can be a monopolar, bipolar, or tripolar electrode. For example, the electrodes can be cuff-type electrodes. An example cuff-type electrode is described in U.S. 2016/0001082 to Butera et al., "SELECTIVE BLOCK OF NERVE ACTION POTENTIAL CONDUCTION," filed Jul. 2, 2015. Cuff-type electrodes are known in the art and are therefore not discussed further herein. Alternatively or additionally, the electrodes can be other types of electrodes known in the art including, but not limited to, microneedle-type electrodes, paddle electrodes, or helical cuff electrodes.

The device can also include a stimulus generator 101. Optionally, the stimulus generator 101 can be implanted in the subject's body. Alternatively, the stimulus generator 101 can be external to the subject's body. The stimulus generator 101 can optionally be battery-powered. The stimulus generator 101 can be operably coupled with the probes 105. This disclosure contemplates that the stimulus generator 101 and the probes 105 can be coupled using any wired, wireless (e.g., radiofrequency (RF)), and/or optical link. The stimulus generator 101 can be configured to provide stimulus signals to the probes 105. As described above, in some implementations, the probes 105 are electrodes. In these implementations, the stimulus generator 101 can be a voltage source or a current source. For example, VBLOC MAESTRO System of ENTEROMEDICS, INC. of St. Paul, Minn. includes an implantable stimulus generator that can be used with the implementations described herein. Alternatively or additionally, the stimulus generator 101 can include programmable logic, e.g., a processor and memory operably coupled to the processor such as the most basic configuration of example computing device 300 of FIG. 3. The programmable logic can be programmed to control operation of the stimulus generator 101. For example, the stimulus generator 101 can be configured to select or adjust the characteristic of the stimulation (e.g., frequency, amplitude, timing, protocol, etc.).

The device can also optionally include a control unit 103. Optionally, the control unit 103 can be implemented as the example computing device 300 of FIG. 3. As shown in FIGS. 1A and 1B, the control unit 103 and the stimulus generator 101 can optionally be separate and distinct units. Optionally, the control unit 103 can be external to the subject' body, i.e., not implanted in the subject's body. The control unit 103 can be operably coupled to the stimulus generator 101 using a communication link. This disclosure contemplates the communication link is any suitable communication link. For example, a communication link can be implemented by any medium that facilitates data exchange between the control unit 103 and the stimulus generator 101 including, but not limited to, wired, wireless, and optical links. Example communication links include, but are not limited to, a LAN, a WAN, a MAN, Ethernet, the Internet, or any other wired or wireless link such as Bluetooth, Wi-Fi, ZigBee, Wi-Max, 3G or 4G. Optionally, the control unit 103 can include a display device and/or an input device (e.g., a human machine interface for receiving user commands). Optionally, the control unit 103 can include an output device, for example, to provide audible, visible, and/or tactile alarms to the user. The control unit 103 can be configured to control operation of the stimulus generator 101. For example, the control unit 103 can be configured to select or adjust the characteristic of the stimulation (e.g., frequency, amplitude, timing, protocol, etc.). Alternatively or additionally, the control unit 103 can be configured to receive set point(s) from a user. For example, a user (e.g., the subject himself or a third person) can use the control unit 103 to program, set or adjust set points at which the stimulus generator turns on/turns off.

Figure 2:
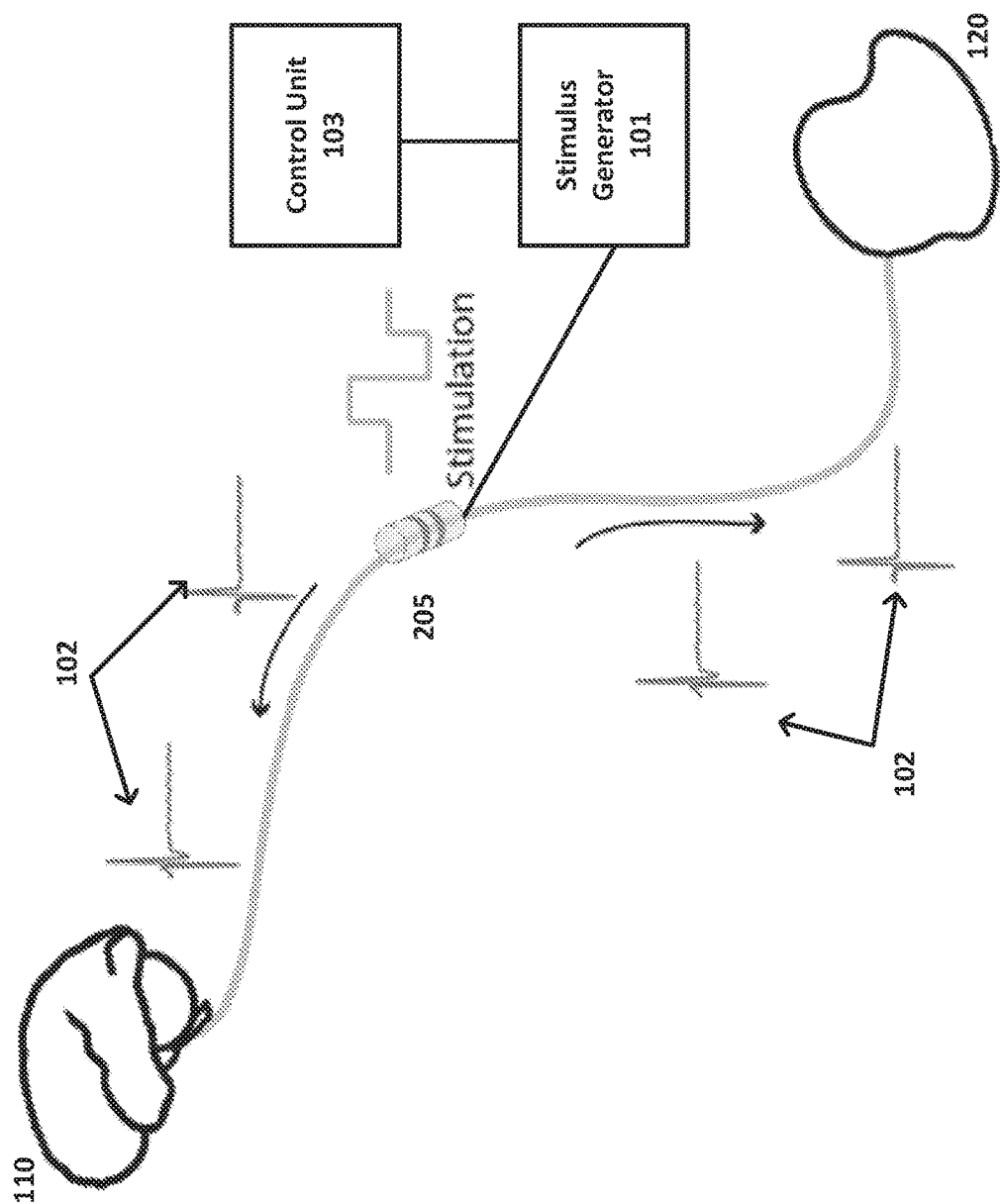
FIG. 2 illustrates a device for stimulation of a subject's nerve according to implementations described herein.

Referring now to FIG. 2, an example device for stimulation of a subject's nerve is shown. FIG. 2 illustrates non-selective activation of both efferent and afferent pathways. The device includes a probe 205, a stimulus generator 101, and a control unit 103. The probe 205 can be configured to deliver at least one of infrared, electrical, thermal, optical, or chemical stimulation to the subject's nerve. Example probes are described above with regard to FIGS. 1A and 1B and are therefore not described in further detail below. Additionally, the stimulus generator 101 and the control unit 103 are described above with regard to FIGS. 1A and 1B and are therefore not described in further detail below. As shown in FIG. 2, a stimulus is delivered via probe 205, and as a result, neurons carry a nerve impulse 102 to the central nervous system and brain 110 and neurons carry a nerve impulse 102 to an organ or muscle 120 (i.e., away from the central nervous system and brain 110). Thus, both efferent and afferent pathways are activated in FIG. 2.

Example Stimulus Signals

As described herein, the stimulation can be at least one of infrared, electrical, thermal, optical, or chemical/pharmacological. The stimulation can be configured to inhibit or activate the subject's nerve. Additionally, stimulation to inhibit neural activity (e.g., both efferent and afferent neural activity) can be paired with stimulation to activate neural activity (e.g., one of efferent or afferent activity). For example, pairing inhibition of neural activity with selective activation of the afferent pathway is shown in FIG. 1A. On the other hand, pairing inhibition of neural activity with selective activation of the efferent pathway is shown in FIG. 1B. FIGS. 1A and 1B are in contrast to FIG. 2, which illustrates non-selective activation of both efferent and afferent pathways.

Selectively activating at least one of efferent or afferent neural activity can be used to modulate physiological processes of the subject. As described below, selective activation of the efferent pathway can be used to modulate the inflammatory response of the subject, for example, to achieve an enhanced inflammatory response. Other example physiological processes include, but are not limited to, metabolism, gastrointestinal function, etc. It should be understood that physiological response of the subject to modulation can be monitored by blood sample, heart rate measurement, or other physiological measurement. For example, when modulating inflammatory response, blood samples can be taken to measure inflammatory cytokines through an assay as described in the examples below. Optionally, this disclosure contemplates balancing a physiological process of the subject via neuromodulation, for example, by balancing afferent and efferent neural activity. For example, in some implementations, parasympathetic and sympathetic activity in obesity can be balanced to impact the progression and development of obesity-related comorbidities. In other implementations, parasympathetic and sympathetic activity in cardiorespiratory disorders can be balanced to stabilize cardiac disorders. It should be understood that obesity and cardiorespiratory disorders are only provided as examples. This disclosure contemplates balancing other physiological processes via neuromodulation. In some implementations, selective activation of at least one of efferent or afferent neural activity can be used to treat a disease or condition of the subject. For example, in some implementations, efferent vagus nerve activity can be selectively activated to remodel and pace cardiac function. In other implementations, afferent vagus nerve activity can be selectively activated to remodel central (brain) circuits. It should be understood that selective activation to remodel cardiac function and/or central circuits are only provided as examples. This disclosure contemplates treating other diseases or conditions by selective activation of neural pathways.

As described above, in some implementations, the stimulus to selectively activate neural activity (e.g., efferent or afferent pathway) can optionally be an electrical signal. In these implementations, the electrical stimulation can optionally have a frequency from about 1 Hz to about 50 Hz and/or deliver a current with an amplitude from about 100 µA to about 2 mA. It should be understood that the electrical stimulation parameters provided above are only examples. This disclosure contemplates using other electrical stimulation parameters configured to activate the efferent or afferent pathway. As described below, neuromodulation can be used to modulate the inflammatory response of the subject. In these implementations, the stimulus to selectively activate neural activity can be cervical vagus nerve stimulation (cVNS), e.g., stimulus applied to the subject's vagal nerve. cVNS stimulation is known in the art, and this disclosure contemplates using stimulation protocols/parameters for cVNS stimulation. Alternatively or additionally, this disclosure contemplates using other modalities to achieve selective activation of neural activity including, but not limited to, infrared, thermal, optical, or chemical/pharmacological stimulation. When using modalities other than electrical stimulation, this disclosure contemplates activating neural activity through invasive (e.g., implanted) or noninvasive (e.g., skin or transcutaneous) probes for delivering infrared, thermal, optical, or chemical/pharmacological stimulation. Additionally, this disclosure contemplates controlling parameters including, but not limited to, stimulation duration, intensity (e.g., temperature, heat, concentration of agent, etc.), and/or frequency.

As described above, in some implementations, the stimulus to inhibit neural activity (e.g., both efferent and afferent pathways) can optionally be kilohertz electrical stimulation (KES). KES is known in the art. For example, KES to achieve nerve block is described in U.S. 2016/0256683 to Butera et al., "GLUCOSE REGULATION VIA ELECTRICAL STIMULATION OF NERVES INNERVATING THE LIVER," filed Mar. 3, 2016. Optionally, the KES can have a frequency from about 1 kHz to about 100 kHz. Optionally, the KES can have a frequency from about 5 kHz to about 50 kHz. Optionally, the KES can deliver a current with an amplitude from about 50 µA to about 50 mA. Optionally, the KES can deliver a current with an amplitude from about 100 µA to about 20 mA. Optionally, KES can have various symmetric or asymmetric waveform shapes including, but not limited to, sine waves, or square waves. It should be understood that the KES parameters provided above are only examples. This disclosure contemplates using other KES parameters configured to inhibit neural activity. Alternatively or additionally, this disclosure contemplates using other modalities to inhibit neural activity including, but not limited to, infrared, thermal, optical, or chemical/pharmacological stimulation. Similar to above, this disclosure contemplates inhibiting neural activity through invasive (e.g., implanted) or noninvasive (e.g., skin or transcutaneous) probes for delivering infrared, thermal, optical, or chemical/pharmacological stimulation. Additionally, this disclosure contemplates controlling parameters including, but not limited to, stimulation duration, intensity (e.g., temperature, heat, concentration of agent, etc.), and/or frequency.

Example Computing Device

It should be appreciated that the logical operations described herein with respect to the various figures may be implemented (1) as a sequence of computer implemented acts or program modules (i.e., software) running on a computing device (e.g., the computing device described in FIG. 3), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 3:
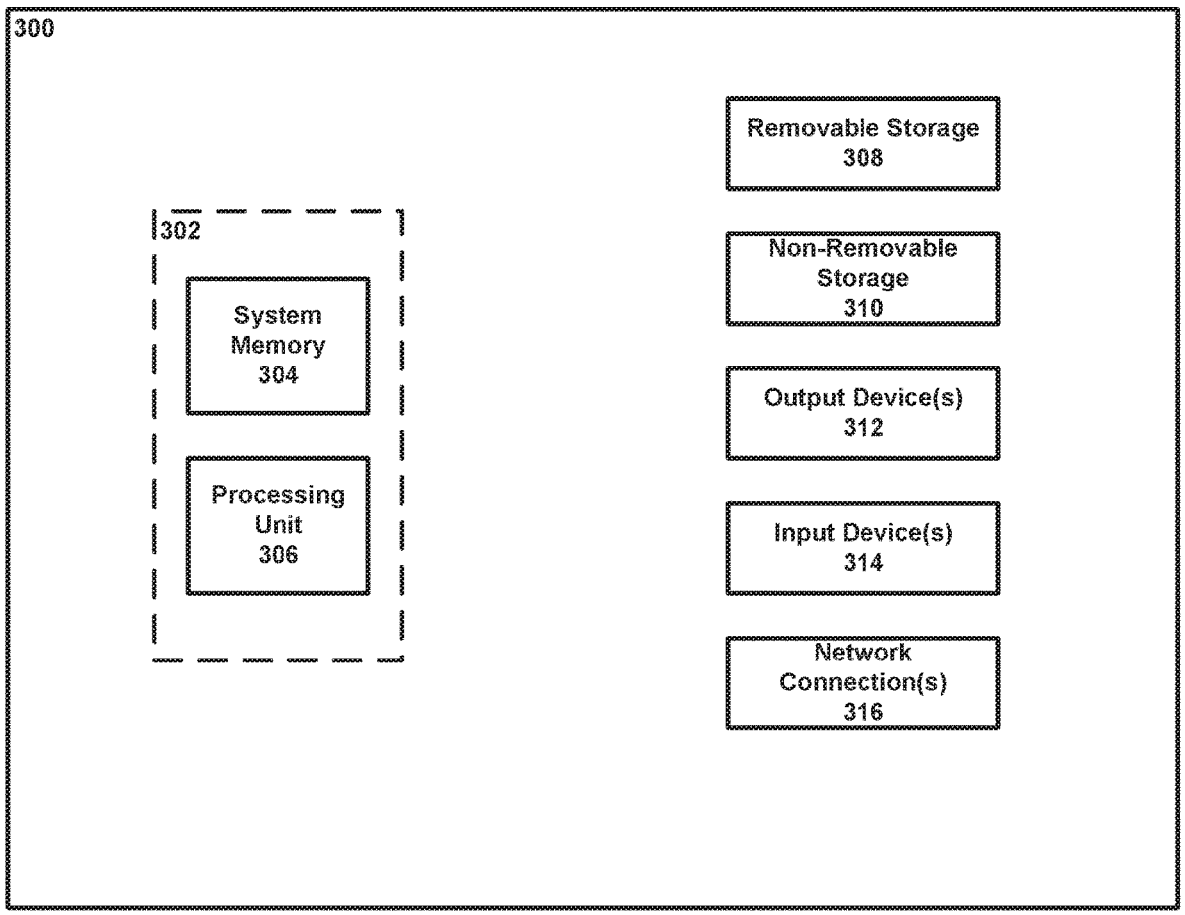
FIG. 3 illustrates an example computing device according to implementations described herein.

Referring to FIG. 3, an example computing device 300 upon which embodiments of the invention may be implemented is illustrated. It should be understood that the example computing device 300 is only one example of a suitable computing environment upon which embodiments of the invention may be implemented. Optionally, the computing device 300 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 300 typically includes at least one processing unit 306 and system memory 304. Depending on the exact configuration and type of computing device, system memory 304 may be volatile (such as random access memory (RAM)), non-volatile (such as read-only memory (ROM), flash memory, etc.), or some combination of the two. This most basic configuration is illustrated in FIG. 3 by dashed line 302. The processing unit 306 may be a standard programmable processor that performs arithmetic and logic operations necessary for operation of the computing device 300. The computing device 300 may also include a bus or other communication mechanism for communicating information among various components of the computing device 300.

Computing device 300 may have additional features/functionality. For example, computing device 300 may include additional storage such as removable storage 308 and non-removable storage 310 including, but not limited to, magnetic or optical disks or tapes. Computing device 300 may also contain network connection(s) 316 that allow the device to communicate with other devices. Computing device 300 may also have input device(s) 314 such as a keyboard, mouse, touch screen, etc. Output device(s) 312 such as a display, speakers, printer, etc. may also be included. The additional devices may be connected to the bus in order to facilitate communication of data among the components of the computing device 300. All these devices are well known in the art and need not be discussed at length here.

The processing unit 306 may be configured to execute program code encoded in tangible, computer-readable media. Tangible, computer-readable media refers to any media that is capable of providing data that causes the computing device 300 (i.e., a machine) to operate in a particular fashion. Various computer-readable media may be utilized to provide instructions to the processing unit 306 for execution. Example tangible, computer-readable media may include, but is not limited to, volatile media, non-volatile media, removable media and non-removable media implemented in any method or technology for storage of information such as computer readable instructions, data structures, program modules or other data. System memory 304, removable storage 308, and non-removable storage 310 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 306 may execute program code stored in the system memory 304. For example, the bus may carry data to the system memory 304, from which the processing unit 306 receives and executes instructions. The data received by the system memory 304 may optionally be stored on the removable storage 308 or the non-removable storage 310 before or after execution by the processing unit 306.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Example Methods

Figure 4:
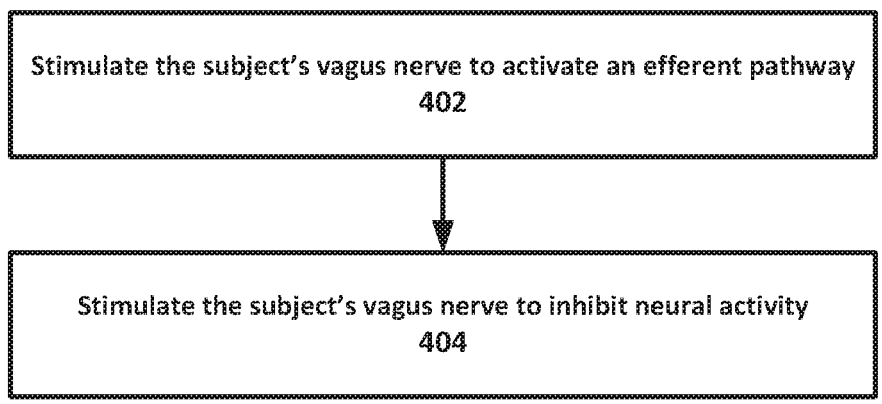
FIG. 4 is a flow chart illustrating example operations for modulating inflammatory response of a subject according to implementations described herein.

Referring now to FIG. 4, a flow chart illustrating example operations for modulating inflammatory processes of a subject is shown. At 402, the subject's vagus nerve is stimulated to activate an efferent pathway. For example, the stimulus can be applied using a probe (e.g., probe 105B in FIG. 1B). The stimulus can optionally be at least one of infrared, electrical, thermal, optical, or chemical/pharmacological stimulation. Optionally, the stimulus to activate neural activity can be efferent cVNS stimulation. At 404, the subject's vagus nerve is stimulated to inhibit neural activity (e.g., both efferent and afferent neural activity). For example, the stimulus can be applied using a probe (e.g., probe 105A in FIG. 1B). The stimulus can optionally be at least one of infrared, electrical, thermal, optical, or chemical/pharmacological stimulation. Optionally, the stimulus to inhibit neural activity can be KES. Paired activation of the efferent pathway and inhibition of neural activity can enhance an anti-inflammatory response of the subject. For example, when neural activity is completely blocked (e.g., using KES) and the efferent pathway is selectively activated (e.g., using ecVNS), TNF-α levels are significantly lower as compared to cases where cVNS stimulation is applied without (or even with partial) nerve block. For example, the anti-inflammatory effects are similar to those achieved when ecVNS is applied after the cVN is transected (cVNx). Thus, anti-inflammatory response is enhanced. The enhanced anti-inflammatory effects of paired inhibition (e.g., using KES) and selective efferent pathway activation (e.g., using ecVNS) are described below with regard to FIGS. 8A-8B, for example. Optionally, pairing activation of the efferent pathway and inhibition of neural activity can balance anti-inflammatory and pro-inflammatory responses of the subject. Alternatively or additionally, a disease or condition of the subject can be treated by modulating inflammatory processes.

Selective activation of the efferent pathway is described above with regard to FIG. 1B. The probe for applying the stimulus to activate the efferent pathway (e.g., probe 105B in FIG. 1B) can be located distally with respect to the probe for applying the stimulus to inhibit neural activity (e.g., probe 105A in FIG. 1B). Both probes interface with the same nerve, e.g., the subject's vagus nerve. Additionally, as described above, the probes can optionally be implanted in the subject's body. Further, as described above, the probes can be different, e.g., a plurality of different probes can be used to deliver the respective stimulus signals.

Alternatively or additionally, the stimulation to inhibit neural activity can achieve a complete block of the subject's vagus nerve. As used herein, a complete block of neural activity means blocking nearly all action potential conduction (also referred to herein as "propagating activity") on a nerve. Optionally, the complete block of the subject's vagus nerve can be a nerve block equivalent to a nerve transection. Complete block can be achieved through stimulation without transection, e.g., in a reversible manner. This disclosure contemplates that the level or degree of nerve block can be determined through measurement. For example, a change in physiological signal (e.g., increasing heart rate) of the subject can provide an indication of the level or degree of nerve block. Alternatively, direct nerve recordings can be used to determine the level or degree of nerve block. Techniques for assessing the level or degree of nerve block using direct nerve recording are known in the art. It should be understood that direct nerve recordings (e.g., stimulus application and response measurement) use time-limited stimulation (e.g., a short pulse or series of pulses), which does not drive a physiological response (e.g., enhancing inflammatory response) of the subject. Alternatively or additionally, the stimulation to inhibit neural activity can be configured to alter a membrane potential of the subject's vagus nerve. This is as opposed to altering membrane excitability of the subject's vagus nerve, for example, as achieved by some chemical/pharmacological agents such as topical agents. KES is an example stimulation protocol that can be used to achieve a complete block of neural activity and/or alter membrane potential of a subject's nerve. It should also be understood that this disclosure contemplates using other modalities to inhibit neural activity including, but not limited to, using infrared, thermal, optical, or chemical/pharmacological stimulation to achieve a complete nerve block.

This disclosure contemplates using various stimulation protocols and/or parameters to pair selective activation of the efferent pathway with inhibition of neural activity. For example, the subject's vagus nerve can be stimulated to activate the efferent pathway during a first period of time, and the subject's vagus nerve can be stimulated to inhibit neural activity during a second period of time. For example, the stimulus to inhibit neural activity can be applied first in time followed by the stimulus to activate efferent activity in some implementations. In other implementations, the stimulus to activate efferent activity can be applied first in time followed by the stimulus to inhibit neural activity. Optionally, in some implementations, the first period of time and the second period of time at least partially overlap. For example, the first period of time and the second period of time can optionally be simultaneous periods of time. In yet other implementations, the first period of time and the second period of time can be different, non-overlapping periods of time.

Figure 5:
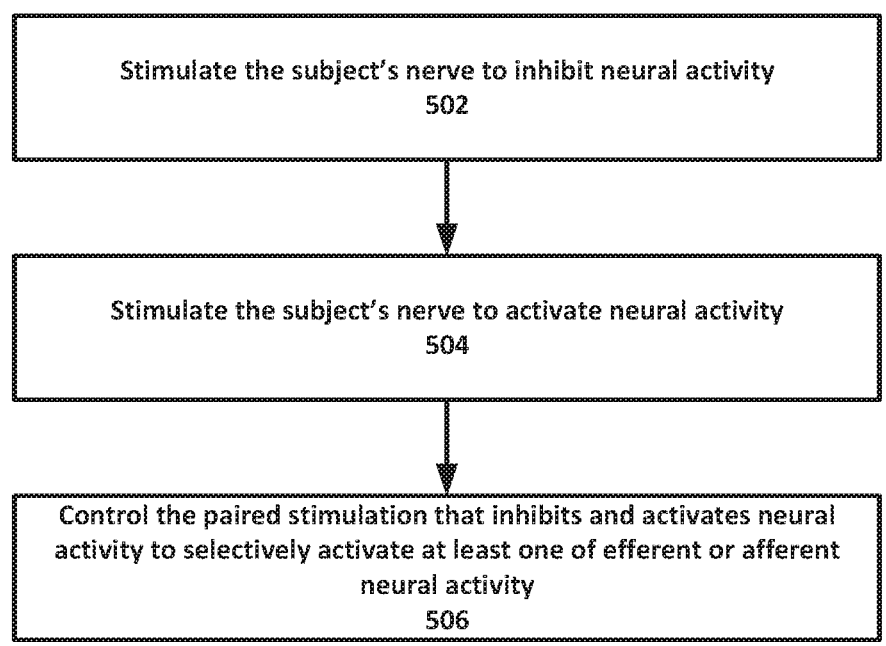
FIG. 5 is a flow chart illustrating example operations for neuromodulation according to implementations described herein

Referring now to FIG. 5, a flow chart illustrating example operations for neuromodulation is shown. At 502, a subject's nerve is stimulated to inhibit neural activity. For example, the stimulus can be applied using a probe (e.g., probe 105B in FIG. 1A or probe 105A in FIG. 1B). The stimulus can optionally be at least one of infrared, electrical, thermal, optical, or chemical/pharmacological stimulation. The subject's nerve can be any central or peripheral nerve. At 504, the subject's nerve is stimulated to activate neural activity. Similar to above, the stimulus can be applied using a probe (e.g., probe 105A in FIG. 1A or probe 105B in FIG. 1B). The stimulus can optionally be at least one of infrared, electrical, thermal, optical, or chemical/pharmacological stimulation. Additionally, both probes interface with the same nerve, and the probes can optionally be implanted in the subject's body. Further, as described above, the probes can be different, e.g., a plurality of different probes can be used to deliver the respective stimulus signals. At 506, the paired stimulation that inhibits and activates neural activity is controlled to selectively activate at least one of efferent or afferent neural activity. As described above, selective activation of the afferent pathway is shown in FIG. 1A, for example, where proximal stimulation is applied to activate the afferent pathway. On the other hand, selective activation of the efferent pathway is shown in FIG. 1B, for example, where distal stimulation is applied to activate the efferent pathway.

As described above, the stimulation to inhibit neural activity can be configured to alter a membrane potential of the subject's nerve. This is as opposed to altering membrane excitability of the subject's nerve, for example, as achieved by some chemical/pharmacological agents such as topical agents. Alternatively or additionally, the stimulation to inhibit neural activity can achieve a complete block of the subject's nerve as described above. KES is an example stimulation protocol that can be used to achieve a complete block of neural activity and/or alter membrane potential of a subject's nerve. It should also be understood that this disclosure contemplates using other modalities to inhibit neural activity including, but not limited to, using infrared, thermal, optical, or chemical/pharmacological stimulation to achieve a complete block. Alternatively or additionally, in some implementations, selective activation of the efferent pathway can be paired with inhibiting neural activity, which results in enhanced anti-inflammatory response of the subject.

Alternatively or additionally, physiological processes (e.g., an inflammatory response) of the subject can be balanced by pairing inhibition of neural activity with selective activation of the efferent or afferent pathway. For example, the efferent and afferent neural activity can be balanced. In some implementations, a disease or condition of the subject is treated by balancing the physiological processes of the subject.

This disclosure contemplates using various stimulation protocols and/or parameters to pair selective activation of the efferent or afferent pathway with inhibition of neural activity. For example, the subject's nerve can be stimulated to activate the efferent or afferent pathway during a first period of time, and the subject's nerve can be stimulated to inhibit neural activity during a second period of time. For example, the stimulus to inhibit neural activity can be applied first in time followed by the stimulus to activate efferent or afferent activity in some implementations. In other implementations, the stimulus to activate efferent or afferent activity can be applied first in time followed by the stimulus to inhibit neural activity. Optionally, in some implementations, the first period of time and the second period of time at least partially overlap. For example, the first period of time and the second period of time can optionally be simultaneous periods of time. In yet other implementations, the first period of time and the second period of time can be different, non-overlapping periods of time.

EXAMPLES

Precise and optimal control of neural circuits requires the ability to stimulate with directional specificity. Directional specificity can be achieved in experimental conditions by nerve transection, however, transections are not viable clinically. As described below, electrical stimulation is paired with kilohertz electrical stimulation (KES) nerve block to selectively stimulate efferent pathways in the rat cervical vagus nerve for modulation of the inflammatory response to endotoxemia. Results demonstrate enhanced anti-inflammatory effects of vagus nerve stimulation when afferent pathways are blocked compared to stimulation paradigms without directional specificity. These results demonstrate a safe and robust method for selective stimulation of vagal afferent and efferent pathways.

Efferent activation of the cervical vagus nerve (cVN) dampens systemic inflammatory processes, potentially modulating a wide-range of inflammatory pathological conditions. In contrast, afferent cVN activation amplifies systemic inflammatory processes, leading to activation of the hypothalamic-pituitary-adrenal (HPA) axis, the sympathetic nervous system through the greater splanchnic nerve (GSN), and elevation of pro-inflammatory cytokines. To clinically implement anti-inflammatory therapy via cervical vagus nerve stimulation (cVNS), one should selectively activate the efferent pathway. Conventional implementations, in animal and clinical investigations, however, activate both afferent and efferent pathways. In the examples, below, cVNS is paired with kilohertz electrical stimulation (KES) nerve block to preferentially activate efferent pathways while blocking afferent pathways. As described below, selective efferent cVNS enhanced the anti-inflammatory effects of cVNS. These results demonstrate that: (i) afferent, but not efferent, cVNS synchronously activates the GSN in a dose-dependent manner; (ii) efferent cVNS enabled by complete afferent KES nerve block enhances the anti-inflammatory benefits of cVNS; and (iii) incomplete afferent KES nerve block exacerbates systemic inflammation. Overall, these data demonstrate the utility of paired efferent cVNS and afferent KES nerve block for achieving selective efferent cVNS, specifically as it relates to neuromodulation of systemic inflammation.

Sinusoidal KES enables a safe, robust, and rapidly reversible block of nerve activity in the cVN. (Reference 7). As described below, KES nerve block can be used to achieve a quick, reliable, and temporary virtual vagotomy for inhibiting activation of afferent pathways while delivering ecVNS. In other words, it is possible to pair inhibition of neural activity using KES with selective activation of the efferent pathway using ecVNS. A KES-enabled virtual vagotomy has many advantages over uncontrollable and irreversible procedures such as nerve transection or pharmacological blockade presently used in both scientific and clinical applications. The techniques provided herein demonstrate a paradigm for selective ecVNS and afferent KES nerve block for suppression of systemic inflammation in response to bacterial lipopolysaccharide (LPS)-induced endotoxemia in a rat animal model (see FIGS. 6A-6C). Both nerve activation and inhibition are quantified below through electrophysiological recordings of peripheral nerve activity along with biochemical changes induced by cVNS and KES nerve block.

The results below demonstrate that when the virtual vagotomy is successfully employed (e.g., a complete nerve block is achieved), the anti-inflammatory benefits of ecVNS are enhanced. In contrast, when the virtual vagotomy is incomplete (e.g., incomplete nerve block), the beneficial effects of ecVNS are only partial. Collectively, these results demonstrate (i) the ability of KES nerve block to provide a method for virtually transecting nerves safely, robustly, and reversibly; (ii) paired delivery of ecVNS and afferent KES nerve block for modulation of systemic inflammatory processes; and (iii) quantitative criteria for evaluating the status of KES nerve block. This technique of paired delivery for achieving selective acVNS or ecVNS may benefit ongoing investigations utilizing cVNS, specifically when developing human bioelectronic medicines based upon laboratory findings.

Afferent cVNS synchronously activates the greater splanchnic nerve. Afferent activation of the cVN has been shown to up-regulate pro-inflammatory signaling via Interleukin-1 beta (IL-1β) expression and activation of the HPA axis through the GSN. (References 8,9). Prior to conducting KES nerve block experiments, a small set of experiments (n=3 rats) were conducted to assess GSN activation as a function of cVNS as well as the effects of acVNS on inflammatory tumor necrosis factor alpha (TNF-α) expression. cVNS was delivered to the left cVN and electroneurogram (ENG) measurements were made from the GSN with biphasic stimulation intensities of 1, 2, and 3 mA (1 Hz, 0.4 milliseconds) (FIG. 6B). A cVNx (i.e., transection of cVN) was performed afterwards on either the cranial or caudal end of the electrode for acVNS or ecVNS. A total of 1000 stimuli were delivered at each amplitude in each configuration to enable detection of the evoked GSN activity. Increasing amplitude evoked GSN potentials with latencies of 5-8 ms were measured during cVNS (FIGS. 7A-7C). A linear fit of the θ calculations revealed a direct relationship between stimulation intensity and evoked GSN activity ($R_2$=0.94). Stimulus-triggered averages from either ecVNS (FIG. 7D) or acVNS (FIG. 7E), along with θ calculations, demonstrated that cVNS-induced activation of the GSN occurs during acVNS only. Biochemical analysis to quantify TNF-α expression (data not shown) demonstrated an increase in serum TNF-α even without LPS delivery.

Paired efferent cVNS and complete afferent KES nerve block enhance anti-inflammatory effects.

cVNS of the intact cVN leads to bidirectional activation of the vagus, as shown through ENG measurements from locations both cranial and caudal to the stimulation electrode (FIG. 8B). Cranial measurements depict two distinct components of the compound action potential (CAP) representing the set of A and C fibers respectively (FIG. 8B). Characterization of θ for each component demonstrates substantial activation of both afferent and efferent pathways. cVNS alone did not demonstrate anti-inflammatory effects in all animals receiving LPS injections. No significant difference was determined between control animals (LPS only) and animals receiving LPS injections with cVNS. In contrast, application of ecVNS following transection of the cVN (i.e., cVNx+ecVNS) resulted in a statistically significant decrease in TNF-α expression (FIG. 8A).

KES nerve block with ecVNS of the intact cVN was used to inhibit activation of afferent pathways while maintaining activation of efferent pathways. ENG measurements from the cranial end of the cVN and biochemical results are shown in FIG. 8B. Complete afferent KES nerve block+ ecVNS (e.g., application of ecVNS to intact cVN paired with application of KES) significantly lowered TNF-α levels compared to control (LPS only), but not compared to cVNx+ecVNS (FIG. 8A) suggesting the presence of a virtual vagotomy of the cVN with KES. ENG measurements from the cranial end of the cVN were used to calibrate and assess the status of afferent KES nerve block. Sample ENG measurements are shown in FIG. 8B, along with the calculated θ values, which indicate complete block of both A and C fiber components. The values at which block was achieved in these experiments, referred to as block thresholds, are depicted in FIG. 9A.

θ was further investigated by analyzing its status throughout the course of the experiment. ENG measurements from each experiment were parsed into 210 trials (see Methods below). θ was calculated for each trial for each experiment, resulting in a time series representation of θ with a sampling interval of 20 seconds. The θ mean±one standard deviation for A and C fiber components across all complete KES nerve block experiments are shown in FIGS. 9B, 9C. For complete KES nerve block experiments, the θ criteria for highly efficacious and complete block was met. Post-experiment evaluation of nerve viability demonstrated components as seen in baseline measurements (FIG. 8B).

Paired efferent cVNS and incomplete afferent KES block lead to pro-inflammatory effects.

Figure 10B:
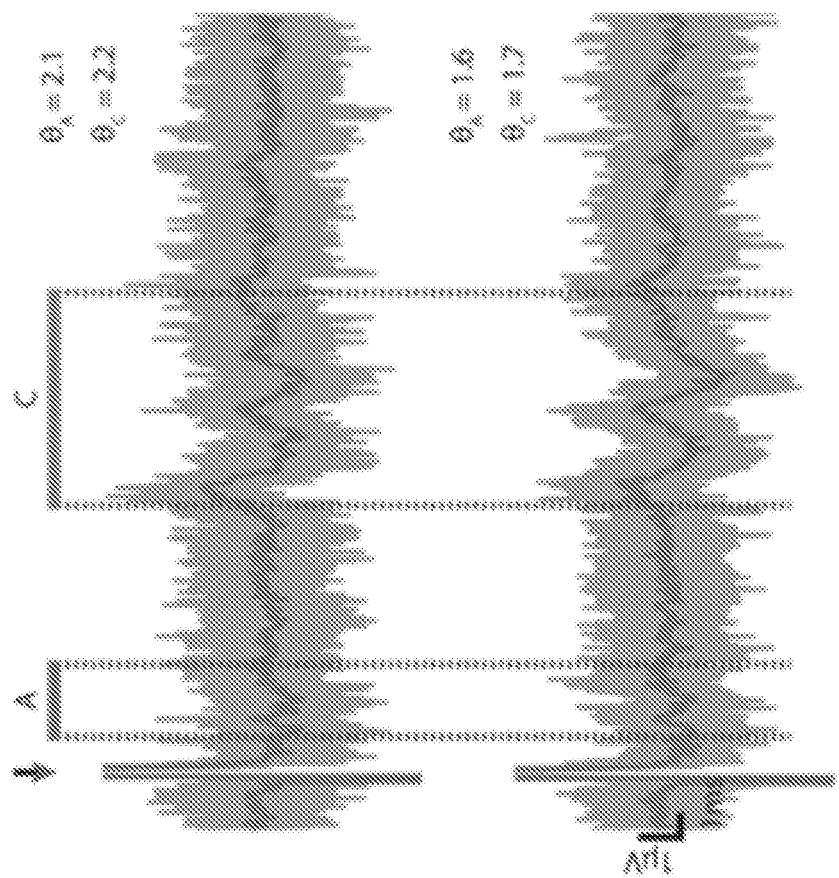
FIGS. 10A and 10B illustrate that incomplete afferent KES nerve block and KES nerve block alone are not sufficient for activating anti-inflammatory pathways.
Figure 10A:
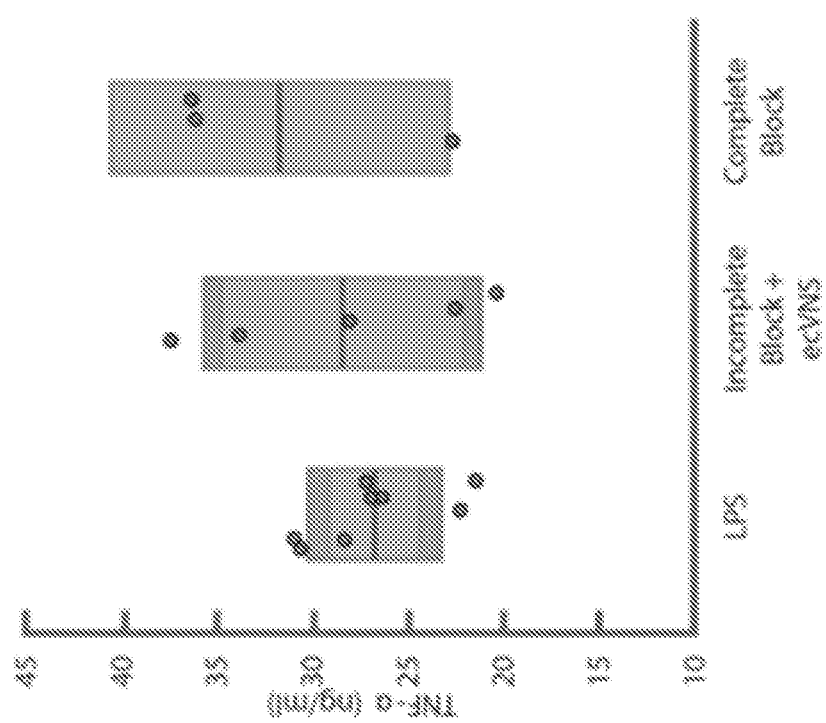

Although the initial calibration tests were successful, a subset of experiments (n=5 rats) were found to be incomplete with respect to afferent KES nerve block. Post hoc analysis revealed that the criteria for complete KES nerve block were not met in these animals, as represented in the sample ENG measurements and calculated θ values shown (FIG. 10B). Both A and C fiber components are present in stimulus-triggered average waveforms. Furthermore, TNF-α expression was elevated in the incomplete KES nerve block experiments to values similar to control (LPS only, FIG. 10A). The block thresholds used in incomplete KES nerve block experiments are shown in FIG. 9A. To investigate why KES nerve block was sometimes incomplete, θ was characterized over the 70 minute experiment period. Time series representations of θ for all incomplete KES nerve block experiments were generated. The θ mean±one standard deviation for A and C fiber components across all incomplete KES nerve block experiments are shown in FIGS. 9D, 9E. Compared to complete KES nerve block, θ time series for incomplete KES nerve block presented a greater mean and standard deviation. No distinguishing features or events were observed suggesting why KES nerve block failed, however.

Virtual vagotomy alone does not provide anti-inflammatory benefits of cVNS. Previous reports demonstrated that animals receiving cVNx and LPS, but not ecVNS, had elevated serum TNF-α, similar to control animals (LPS only). (Reference 1). For comparison, serum in animals receiving complete KES nerve block and LPS, but no ecVNS, were characterized. Complete KES nerve block was verified using the aforementioned procedures and the same experimental protocol (FIG. 6C) was carried out. ELISA results (FIG. 10A) showed elevated serum TNF-α levels, similar to those previously reported in cVNx animals. (Reference 1).

Discussion

Suppression of systemic and local inflammation via ecVNS has the potential to be a powerful clinical strategy. When used on the bench top, investigations typically transect and stimulate the peripheral end of the vagus. In this study, the ability to conduct a virtual vagotomy via KES nerve block has been demonstrated, which is feasible in clinical settings. The primary results are that (1) KES can block evoked nerve activity that is equivalent to nerve transection and (2) KES nerve block alone is insufficient for activating the vagal anti-inflammatory pathways. These results have important clinical implications, as it allows for unidirectional electrical activation of the vagus nerve without the need to transect the nerve.

Results from previous investigations have demonstrated activation of the GSN during cVNS as well as the role of the GSN in regulating inflammation. (References 9, 10). However, previous investigations are qualitative and only demonstrates the presence of an event upon supramaximal stimulation. Activation of the GSN during cVNS using stimulation intensities (1-3 mA virus 0.5-2.0 mA) that are commonly used in clinical applications of cVNS have been quantified. (References 12,13). Stimulation parameters described herein differ from those used clinically with respect to pulse width (0.4 ms versus 0.25 ms) and frequency (1 Hz versus 10-20 Hz). A direct relationship was found between cVNS stimulation intensity and the resulting sympathetic activation. Transection of the nerve at either cranial or caudal ends of the stimulating electrode revealed that this activation is predominantly due to activation of afferent pathways (FIGS. 7A-7E). These results suggest that increased stimulation intensities result in greater activation of the GSN, which carries sympathetic activity to a majority of visceral organs responsible for maintenance of homeostasis. It has been shown that chronic SNS activity drives local persistent inflammation leading to deleterious side effects like cachexia and increased blood pressure. (References 14,15). Thus, while direct activation of the sympathetic splenic and splanchnic nerves can offset inflammation, chronic activation of the GSN in patients receiving cVNS is not a clinically viable strategy.

The results described herein show that applying KES nerve block as a tool for achieving a virtual vagotomy and selective efferent stimulation is a viable clinical tool. Furthermore, a robust method and criterion, called block efficacy, for evaluating the status of KES nerve block has been established. This approach enables quantitative validation and evaluation of the effects of KES nerve block. Quantification of block efficacy throughout the experiment (FIG. 9B-9E) enables detection of changes in block efficacy and thresholds during application. No significant differences were observed in the experimental cases.

In the study described herein, a post-hoc assessment of nerve viability was conducted as a binary test for ensuring continued conduction of nerve activity post-KES delivery. Post-hoc assessment (described in Methods section) was conducted in each experiment but limited in time due to the need for blood collection. In each experiment, post-hoc assessment successfully resulted in ENG measurements not significantly different than baseline ENG measurements (FIG. 8B).

It has been previously demonstrated that the ability to use KES nerve block for selective block of A or C fiber components in mammalian and amphibian animal models. (References 7, 16). The current investigation employed KES nerve block as an all-or-none technique. It should be noted, however, that the use of selective KES nerve block may be useful in cases where selective block of A or C fiber activity is desired. Moreover, the mammalian cVN consists of fibers from A, B, and C fiber classes. (Reference 17). The experimental setup, limited by exposed nerve length and electrode spacing, allowed investigation of only A and C fiber components at a macro scale. To validate block of all fiber classes and sub-types, along with selective KES nerve block, larger animal models in which a greater exposed nerve length is attainable can be completed.

In a subset of experiments (n=5), post-hoc analysis revealed that block was incomplete (FIGS. 10A, 10B), resulting in increased serum TNF-α. Although calibration was conducted in each experiments to determine block threshold for each experiment (FIG. 9A), and ENG measurements were visualized online, it is possible that failure to maintain block could have occurred from changes at the electrode-tissue interface or stimulation equipment. While it is possible for direct current (DC) to contaminate the effects of KES nerve block, it is unlikely because equipment was calibrated prior to starting KES nerve block. Furthermore, DC contamination leads to damage of nervous tissue and can result in uncontrolled and unwanted amounts of either DC stimulation or DC nerve block. (Reference 18).

The experimental methods and data analysis methods used in the study described herein suggest one potential framework for clinical use of KES nerve conduction block. First, application of KES nerve conduction block with a valid readout with temporal dynamics on the order of milliseconds may be beneficial. ENG measurements from the cVN were used to directly assess the effects of KES nerve conduction block on evoked cVN activity. Without such a readout, selection of the appropriate KES amplitudes and thresholds may be difficult. Second, a baseline of what activity is to be blocked can be be set. In the present study, the RMS voltage of evoked CAPs was used as the activity to block. Finally, the required duration of KES nerve block must be known for each nerve and physiological function of interest. These three elements may be incorporated into an implantable device for chronic use, or could be utilized acutely in patients through on-nerve electrodes with percutaneous leads.

One side-effect previously reported during application of KES nerve block is an initial brief period of asynchronous activation of the nerve. (References 7,16,19). This response, coined the onset response, is typically short lived (<100 ms) and occurs immediately after initiating KES nerve block. This asynchronous activation is removed from the recordings described herein by the online filtering and post-hoc stimulus-triggered averaging of ENG measurements. Although not measured in the experiments described herein, it is possible that the onset response was present in the form of laryngeal muscle activation. On-going investigations can be used to quantify laryngeal activation during KES nerve block of the vagus.

The results presented herein utilized the standard protocol for investigating neuromodulation of systemic inflammation on the left cVN. Additional pilot experiments (unpublished) were carried out to investigate the effects of bilateral cVNS and KES nerve block. These data suggest that no additional benefit could be achieved through bilateral neuromodulation similar to previous reports. (Reference 20). A pilot study to investigate the necessity of the pre-stimulation period for down-regulation of systemic inflammation was also conducted. Animals were subject to the same stimulation protocol described above, but without the pre-stimulation period. These additional data suggest that the pre-stimulation period has little to no effect on modulation of LPS-induced systemic inflammation.

Systemic inflammation can be modulated through cVNS, as shown by this report and others. How exactly the nervous system modulates systemic inflammation is a topic currently undergoing significant scientific inquiry. It is valuable to highlight knowns and unknowns about the mechanism of action for modulation of systemic inflammation through cVNS. The cholinergic anti-inflammatory pathway posits that the vagus nerve is the efferent arm of the inflammatory reflex. The hypothesized mechanism is that parasympathetic efferent fibers in the vagus nerve innervate postganglionic sympathetic splenic neurons in the celiac ganglia with axons in the splenic nerve. Stimulation of efferent cVN pathways leads to modulation of the postganglionic splenic neurons and results in suppression of splenic TNF-α production. This mechanism of action has received significant debate due to evidence from anatomical investigations demonstrating little or no direct cholinergic vagal innervation of the spleen (Reference 21), from physiological studies demonstrating the need for intact GSN and splenic nerve (Reference 22), and electro-physiological studies, including this report (FIGS. 7A-7E), showing no measurable connection between ecVNS, the GSN, or the splenic branch of the GSN (Reference 10).

Alternative hypotheses related to mechanism exist, such as the vagus nerve controls splenic nerve activity in an indirect manner through CNS reflex, but not by a direct efferent VN pathway. (Reference 10). In addition, there is the possibility that the effects of cVNS could be of non-physiological origin, and due to activation of afferent and efferent pathways in synchronous or asynchronous manners that drive physiological function to its limits. These contrasting mechanistic and functional results can be the subject of further investigation into the mechanism of action, especially as cVNS is utilized in clinical settings for long-term treatment of inflammatory conditions.

Methods

Animal Preparation. All animal care and procedures were reviewed and approved by the Institutional Animal Care and Use Committee at The Georgia Institute of Technology and all methods were performed in accordance with the relevant guidelines and regulations. In vivo experiments were carried out on the left cVN and GSN in adult male Sprague-Dawley rats (Charles River). Animals (311±50 g, n=65) were anesthetized in a chamber using 5% isoflurane (1 liter/min flow rate). Once recumbent, the animal was maintained at 2-3% isoflurane for 45 minutes, and then at 1.5% isoflurane for the remainder of the experiment. Body temperature was monitored and maintained at 37-40° C. with a rectal temperature probe (TM-3, Warner Instruments, Hamden, Conn.) and warming pad (COM-11289, SparkFun Electronics, Niwot, Colo.). Depth of anesthesia was evaluated by pinching the rear footpad. When there was no response, the animal's neck was shaved and depilated. A midline incision was made and the skin and subcutaneous muscles tissues were retracted via blunt dissection. The salivary glands, sternocleidomastoideus, and omohyoideus were repositioned to allow access to the carotid sheath. The cVN and the common carotid artery were separated using a dissection microscope providing a total exposed cVN length of 1.2-1.4 cm.

For studies requiring access to the GSN, the dorsal surface of the animal was prepared using the same preparation techniques above. An incision was made approximately 1 cm caudal to the 6th false rib and approximately 0.5 cm lateral to the spinous processes. The skin, underlying muscles, and latissiumus dorsi were blunt dissected and retracted. The suprarenal gland was identified and blunt dissected apart from the surrounding fat layers. The adrenal nerve was identified and followed proximally to the suprarenal ganglia, which is the proximal end of the greater splanchnic nerve. The greater splanchnic was isolated from surrounding fat and connective tissue. Electrodes (described below) were placed on the cVN for stimulation, block, and recording of nerve activity and, when desired, a recording electrode was placed on the GSN (FIG. 6B). Nerves were not desheathed or dissected. Animals were euthanized at the end of the experiment by thoracotomy done to collect a cardiac blood sample.

Electrophysiology. All experiments were conducted in a Faraday cage with an electrically floating setup powered by an uninterruptible power supply. A floating ground was established by a 20 G needle inserted into the right gastrocnemius muscle and connected to the table. Control of experimental hardware, delivery of stimuli, and data acquisition were all achieved using The Real-Time eXperiment Interface (RTX123). Custom, bi-polar electrodes were made in-house to stimulate, record, and block activity from the cVN and GSN. In brief, braided stainless steel wires (#793500, A-M Systems, Sequim, Wash.) were threaded through silicone tubing (#807600, A-M Systems, Sequim, Wash.), spot-welded to platinum-iridium contact pads and the outer surface of the cuff coated with polydimethylsiloxane (PDMS) for electrical insulation. Electrode impedance (1.2±0.6 kΩ) was characterized at 1 kHz using an impedance conditioning module (FHC Inc., Bowdoin, Me.). Both electrical and mechanical characteristics were evaluated prior to electrode reuse. For cVN preparations, the electrode spacing was minimized between the stimulation and block electrodes (0.2±0.1 cm), and maximized between the recording and block electrodes (1.0±0.1 cm).

ENG measurements were differentially measured and amplified with a gain of 104× and filtered with a band-pass of 102-104 Hz (SR560, Stanford Research Systems, Sunnyvale, Calif.) prior to being digitized at 20 kHz (PCIe-6259, National Instruments, Austin, Tex.). Biphasic constant current pulses (1 mA, 0.4 ms, 1 Hz) for nerve stimulation were generated using the RTXI signal generator module and optically-isolated using a linear stim-ulus isolator (A395, WPI, Sarasota, Fla.) prior to being delivered to the stimulation electrode. Block of nerve activity was achieved using kilohertz electrical stimuli (KES, ref. 7) generated by a function generator (AFG 3021, Tektronix, Beaverton, Oreg.). The function generator output was optically-isolated using an analog stimulus isolator (Model 2200, A-M Systems, Sequim, Wash.) prior delivery to the block electrode. KES frequencies and amplitudes were chosen based upon previously demonstrated values for complete block of cVN activity7. Timing of KES delivery was controlled by gating the function generator output using RTXI. All stimulus isolation units used were calibrated prior to each experiment and output offsets zeroed by visualization on an oscilloscope. The complete cVN electrophysiological setups used in this study are shown in FIGS. 6A-6C.

Blood collection. Approximately 5 ml of blood was collected from the left ventricle of the heart at the end of each experiment. Blood was allowed to clot at room temperature for 15 minutes prior to centrifugation at 2000 g for 20 minutes.

LPS-induced endotoxemic shock. LPS (L2630, Sigma Aldrich) was freshly prepared the morning of each experiment by dissolving in sterile, deionized water followed by a 15 minute sonication at 37° C. Animals were injected intravenously via a 24 G catheter inserted in the tail vein with a dose of 15 mg/kg in a total volume of 1 ml.

Experimental Protocols. LPS-induced endotoxemic shock. All experiments followed a standard protocol for induction of endotoxemic shock and delivery of paired efferent stimulation and block (FIG. 6C). Animals first received 10 minutes of stimulation or paired stimulation and block (pre-stim). Upon completion, animals received either LPS or saline tail vein injections, and another 10 minutes of stimulation or paired stimulation and block were delivered (post-stim). KES block was continued through the duration of the experiment. Blood col-lection took place 50 minutes after the completion of the post-stim period. Recordings of cVN activity were made during the entire experiment to validate KES block of afferent activity.

Nerve transection studies. The cVN was transected (cVNx) in a subset of studies to characterize the effects of afferent (n=2, data not shown) and efferent (n=6) cVNS on the systemic response to endotoxemic shock. A cuff electrode (described above) was placed around the cVN for stimulation prior to transection. Once the cuff was secured in place, the cranial or caudal end of the nerve were cut. The nerve was stimulated pre- and post-LPS injection, and blood was collected 50 minutes after the end of the post-stim period. In addition, GSN activity was measured while stimulating the cranial or caudal ends of the transected cVN.

Nerve block experiments. It has been previously reported KES (sinusoidal) nerve block inhibited evoked potentials in the cVN, and characterized the response of the cVN to KES as a function of both KES frequency and amplitude. Based upon these findings, a KES frequency of 40 kHz with amplitudes in the range of 1.5-2.0 $mA_{peak}$ were used, A calibration trial was conducted to determine the specific KES amplitude for use in each experiment. The nerve was stimulated at a rate of 1 Hz and online ENG measurements were used as a readout to assess the status of KES nerve block. KES amplitudes started at 1.5 mApeak and were increased in steps of 0.1 $mA_{peak}$ until the block threshold was identified. Both stimulation and block were turned off after identification of the block threshold. Calibration procedures lasted approximately 30-45 seconds in each experiment. Post-experiment visualization and electrophysiological assessment of nerve viability were conducted by delivering 5-10 stimulating pulses and observing evoked CAPs, along with monitoring for nerve or electrode discoloration. From all experiments con-ducted, nerve discoloration, but not loss of nerve conduction, was observed in 2 animals with incomplete KES nerve block and have been removed from the data pool.

Data Analysis. ENG Analysis. ENG measurements were used to quantify cVNS activation and to validate the status of afferent block. All data processing and analysis was conducted in MATLAB (R2015b, MathWorks, Inc. Natick, Mass.). ENG recordings from the cVN and GSN were digitally band-pass filtered (100 to 3000 Hz) prior to being stimulus-triggered to generate average waveforms (20 runs per trial), resulting in a total of 210 trials per experiment. All waveforms shown in this report are averages of 20 runs unless stated otherwise. In the experimental setup, only A and C components from stimulus-triggered average waveforms were distinguishable due to limitations in electrode-to-electrode distance. Time windows were computed using the electrode-to-electrode distance measured in the experimental setup and component-specific conduction velocities (A>2.0 m/s, C<2.0 m/s) for quantification of evoked components. Windows were calculated for the A and C fiber components, along with a 10 ms pre-stimulus noise window. Window bounds were set to exclude stimulus and amplifier artifacts. The root mean square (RMS) value of each window was computed using the MATLAB signal processing toolbox (rms function). The signal-to-noise ratio, represented by θ, for each CAP component was calculated by taking the RMS value for a given component (A or C) and dividing by the RMS value of the noise window. (References 24,25). The use of a windowed RMS metric, as opposed to peak analysis, incorporates the temporal dynamics of different CAP components and provides a more complete view of nerve activation or block. For example, small, slow-conducting fibers (e.g., C-fibers) appear as temporally dispersed waveforms which would not be captured by time of occurrence and magnitude of peaks alone.

Quantification of KES nerve block efficacy and nerve activation. Both KES nerve block efficacy and nerve activation were quantified to enable quantitative evaluation of neurostimulation and block effects on TNF-α expression. To quantify the efficacy of KES nerve block and for statistical analysis, the standard signal-to-noise formulation was adopted to generate a scalar measure that quantifies the efficacy of KES nerve block, which is referred to and represent by Σ. The formal calculation is:

$$\Sigma_{i,j}=V_{rms}(i)/V_{rms}(j_{noise}), i \in (A_\alpha, A_\beta, A_\delta, A_\gamma, B, C) \quad (1)$$

where $\Sigma_{i,j}$ represents the block efficacy for a measurable and recognizable compound action potential (CAP) component, i, in the jth trial, and the RMS values are of filtered single trial or stimulus-triggered average waveforms. This leads to the following classification scheme:

$$\Sigma=\text{high/complete block, if } \Sigma_{i,j} \leq 1 \pm V_{rms}(j_{noise})/2$$

$$\Sigma=\text{low/incomplete block, if } 1+V_{rma}(j_{noise})/2<\Sigma_{i,j}<\max(\Sigma_{i,j}) \quad (2)$$

Half of the RMS noise is included in the analysis to account for variations in experimental setup, differences in electrode-tissue coupling, and aliased noise from the KES waveform and stimulation equipment. This is equivalent to adding half of the standard deviation of the noise, since all ENG measurements are band-pass filtered and exclude DC components. The upper bound, $\max(\Sigma_{i,j})$, ideally set from a baseline trial in which KES is not delivered to the nerve. The same formulation (Eqn. 1) is used without the classification scheme for quantifying nerve activation. Nerve activation values are referred to and represented by θ herein. When θ<1, nerve activation is non-existent with the ENG measurement methods. In the current experimental setup, only A and C components from stimulus-triggered average waveforms were distinguishable due to limitations in electrode-to-electrode distance, however this metric can expand to the larger set of CAP components.

Biochemical Analysis. Serum TNF-α concentrations were quantified using commercially available ELISA kits (BD Biosciences). Calibration curves were generated and TNF-α concentrations were obtained by measuring absorbance at 450 nm.

Statistical Analysis. Analysis of variance and t-tests were performed using the MATLAB statistics toolbox (anova1, ttest2 functions). The Jarque-Bera tests (jbtest function) was used to evaluate normality of experimental groups. All statistical tests were carried out with α=0.05. All box plots show the 95% confidence interval (pink) for the mean (center bar) and 1 standard deviation (blue).

REFERENCES

1. Borovikova, L. V. et al. Vagus nerve stimulation attenuates the systemic inflammatory response to endotoxin. Nature 405, 458-462 (2000).

2. Rosas-Ballina, M. et al. Splenic nerve is required for cholinergic antiinflammatory pathway control of TNF in endotoxemia. Proceedings of the National Academy of Sciences of the United States of America 105, 11008-13 (2008).

3. Martelli, D., McKinley, M. & McAllen, R. The cholinergic anti-inflammatory pathway: A critical review. Autonomic Neuroscience: Basic and Clinical 182, 65-69 (2014).

4. Prechtl, J. & Powley, T. The fiber composition of the abdominal vagus of the rat. Anatomy and Embryology 181, 101-115 (1990).

5. Powley, T. L., Prechtl, J. C., Fox, E. A. & Berthoud, H. R. Anatomical considerations for surgery of the rat abdominal vagus: distribution, paraganglia and regeneration. Journal of the Autonomic Nervous System 9, 79-97 (1983).

6. Berthoud, H. R. & Powley, T. L. Characterization of vagal innervation to the rat celiac, suprarenal and mesenteric ganglia. Journal of the Autonomic Nervous System 42, 153-169 (1993).

7. Patel, Y. A. & Butera, R. J. Differential fiber-specific block of nerve conduction in mammalian peripheral nerves using kilohertz electrical stimulation. Journal of Neurophysiology 113, 3923-9 (2015).

8. Hosoi, T., Okuma, Y. & Nomura, Y. Electrical stimulation of afferent vagus nerve induces IL-1beta expression in the brain and activates HPA axis. American Journal of Physiology Regulatory, Integrative and Comparative Physiology 279, R141-R147 (2000).

9. Martelli, D., Yao, S. T., McKinley, M. J. & McAllen, R. M. Neural control of inflammation by the greater splanchnic nerves. Temperature 1, 14-15 (2014).

10. Bratton, B. O. et al. Neural regulation of inflammation: no neural connection from the vagus to splenic sympathetic neurons. Experimental Physiology 97, 1180-5 (2012).

11. Martelli, D., Yao, S. T., McKinley, M. J. & McAllen, R. M. Reflex control of inflammation by sympathetic nerves, not the vagus. The Journal of Physiology 592, 1677-86 (2014).

12. Labiner, D. M. & Ahern, G. L. Vagus nerve stimulation therapy in depression and epilepsy: therapeutic parameter settings. Acta neurologica scandinavica 115, 23-33 (2007).

13. Koopman, F. A. et al. Vagus nerve stimulation inhibits cytokine production and attenuates disease severity in rheumatoid arthritis. Proceedings of the National Academy of Sciences 113, 8284-8289 (2016).

14. Laviano, A. et al. Neural control of the anorexia-cachexia syndrome. American Journal of Physiology Endocrinology And Metabolism 295, 1000-1008 (2008).

15. Brooks, S. L., Neville, A. M., Rothwell, N. J., Stock, M. J. & Wilson, S. Sympathetic activation of brown-adipose-tissue thermogenesis in cachexia. Bioscience Reports 1, 509-517 (1981).

16. Joseph, L. & Butera, R. J. High-frequency stimulation selectively blocks different types of fibers in frog sciatic nerve. IEEE Transactions on Neural Systems and Rehabilitation Engineering 19, 550-557 (2011).

17. Agostoni, E., Chinnock, J. E., Daly, M. D. B. & Murray, J. G. Functional and histological studies of the vagus nerve and its branches to the heart, lungs and abdominal viscera in the cat. The Journal of Physiology 135, 182-205 (1957).

18. Franke, M., Bhadra, N., Bhadra, N. & Kilgore, K. Direct current contamination of kilohertz frequency alternating current waveforms. Journal of Neuroscience Methods 232, 74-83 (2014).

19. Miles, J. D., Kilgore, K. L., Bhadra, N. & Lahowetz, E. Effects of ramped amplitude waveforms on the onset response of high-frequency mammalian nerve block. Journal of Neural Engineering 4, 390-398 (2007).

20. Willemze, R. A., Luyer, M. D., Buurman, W. A. & de Jonge, W. J. Neural reflex pathways in intestinal inflammation: hypotheses to viable therapy. Nature Reviews Gastroenterology & Hepatology 12, 353-362 (2015).

21. Nance, D. M. & Sanders, V. M. Autonomic Innervation and Regulation of the Immune System (1987-2007). Brain, Behavior, and Immunity 21, 736-745 (2007).

22. Huston, J. M. et al. Splenectomy inactivates the cholinergic antiinflammatory pathway during lethal endotoxemia and polymicrobial sepsis. The Journal of Experimental Medicine 203, 1623-8 (2006).

23. Lin, R. J., Bettencourt, J., White, J. A., Christini, D. J. & Butera, R. J. Real-time Experiment Interface for biological control applications. In 2010 Annual International Conference of the IEEE Engineering in Medicine and Biology Society, EMBC'10, 4160-4163 (2010).

24. Yoo, P. B. et al. High-resolution measurement of electrically-evoked vagus nerve activity in the anesthetized dog. Journal of Neural Engineering 10, 1-9 (2013).

25. Chu, J.-U. et al. Improvement of signal-to-interference ratio and signal-to-noise ratio in nerve cuff electrode systems. Physiological Measurement 33, 943-67 (2012).

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method for modulating inflammatory processes of a subject, comprising:
    applying a first stimulus signal to a nerve of the subject's to activate an efferent pathway;
    applying a second stimulus signal to the nerve to inhibit neural activity to achieve a complete block; and
    treating an inflammatory condition of the subject by coordinating application of the first and second stimulus signals, wherein pairing activation of the efferent pathway and inhibition of neural activity enhances an anti-inflammatory response of the subject.

2. The method of claim 1, wherein the nerve is the subject's vagus nerve.

3. The method of claim 1, wherein the complete block comprises a nerve block equivalent to a nerve transection.

4. The method of claim 1, wherein the stimulation to inhibit neural activity is configured to alter a membrane potential of the nerve.

5. The method of claim 1, wherein treating an inflammatory condition of the subject by coordinating application of the first and second stimulus signals comprises balancing anti-inflammatory and pro-inflammatory responses of the subject.

6. The method of claim 1, wherein applying the first stimulus signal to the nerve to activate the efferent pathway comprises applying at least one of infrared, electrical, thermal, optical, or chemical stimulation.

7. The method of claim 6, wherein applying the first stimulus signal to the nerve to activate the efferent pathway comprises applying electrical stimulation.

8. The method of claim 1, wherein applying the second stimulus signal to the nerve to inhibit neural activity comprises applying at least one of infrared, electrical, thermal, optical, or chemical stimulation.

9. The method of claim 8, wherein applying a second stimulus signal to the nerve to inhibit neural activity comprises applying kilohertz electrical stimulation (KES).

10. The method of claim 9, wherein the KES has a frequency from about 1 kHz to about 100 kHz.

11. The method of claim 9, wherein the KES delivers a current with an amplitude from about 50 µA to about 50 mA.

12. The method of claim 1, wherein the nerve is stimulated to activate the efferent pathway during a first period of time, and the nerve is stimulated to inhibit neural activity during a second period of time.

13. The method of claim 12, wherein the first period of time and the second period of time at least partially overlap.

14. The method of claim 13, wherein the first period of time and the second period of time are simultaneous.

15. The method of claim 12, wherein the first period of time and the second period of time are different, non-overlapping periods of time.

16. A device for modulating inflammatory processes of a subject, comprising:
    a first probe configured to interface with a nerve of the subject;
    a second probe configured to interface with the nerve;
    a stimulus generator operably coupled with the first probe and the second probe, the stimulus generator being configured to provide stimulus signals to the first probe and the second probe; and
    a control unit operably coupled with the stimulus generator, the control unit comprising a processor and memory operably coupled to the processor, the memory having computer-executable instruction stored thereon that, when executed by the processor, cause the control unit to control the stimulus generator to:
    provide a first stimulus signal configured to activate an efferent pathway of the nerve;
    provide a second stimulus signal configured to inhibit neural activity of the nerve to achieve a complete block; and
    coordinate delivery of the first and second stimulus signals to treat an inflammatory condition of the subject, wherein pairing activation of the efferent pathway and inhibition of neural activity is configured to enhance an anti-inflammatory response of the subject.

17. The device of claim 16, wherein the memory has further computer-executable instruction stored thereon that, when executed by the processor, cause the control unit to:
    receive a measure of the subject's inflammatory response; and
    use the measure of the subject's inflammatory response to coordinate delivery of the first and second stimulus signals to treat the inflammatory condition of the subject.

18. The device of claim 17, wherein the measure of the subject's inflammatory response is a measure of inflammatory cytokines.

19. The device of claim 16, wherein the first and second probes are electrodes.

20. The device of claim 16, wherein the stimulation to inhibit neural activity is configured to alter a membrane potential of the nerve.

21. The device of claim 16, wherein the nerve is the subject's vagus nerve.

* * * * *

UNITED STATES PATENT AND TRADEMARK OFFICE
CERTIFICATE OF CORRECTION

PATENT NO. : 10,981,007 B2  
APPLICATION NO. : 16/301054  
DATED : April 20, 2021  
INVENTOR(S) : Yogi Anil Patel et al.

Page 1 of 1

It is certified that error appears in the above-identified patent and that said Letters Patent is hereby corrected as shown below:

In the Claims

Column 25, Line 37 for Claim reference numeral '1', "applying a first stimulus signal to a nerve of the subject's" should read --applying a first stimulus signal to a nerve of the subject--

Signed and Sealed this  
Sixth Day of July, 2021

Drew Hirshfeld  
*Performing the Functions and Duties of the*  
*Under Secretary of Commerce for Intellectual Property and*  
*Director of the United States Patent and Trademark Office*